(12) United States Patent
Mullineaux et al.

(10) Patent No.: US 8,445,747 B2
(45) Date of Patent: May 21, 2013

(54) PLANT RESPONSES

(75) Inventors: Phil Mullineaux, Colchester (GB);
Ulrike Bechtold, Colchester (GB)

(73) Assignee: Plant Bioscience Limited, Norfolk (GB)

( * ) Notice: Subject to any disclaimer, the term of this patent is extended or adjusted under 35 U.S.C. 154(b) by 226 days.

(21) Appl. No.: 12/531,349

(22) PCT Filed: Mar. 17, 2008

(86) PCT No.: PCT/GB2008/050186
§ 371 (c)(1),
(2), (4) Date: Jan. 28, 2010

(87) PCT Pub. No.: WO2008/110848
PCT Pub. Date: Sep. 18, 2008

(65) Prior Publication Data
US 2010/0138958 A1    Jun. 3, 2010

(30) Foreign Application Priority Data
Mar. 15, 2007   (GB) ................................ 0704984.4

(51) Int. Cl.
*A01H 5/00*     (2006.01)
*C12N 15/63*    (2006.01)
*C12N 15/82*    (2006.01)

(52) U.S. Cl.
USPC ........ 800/290; 800/278; 435/468; 435/320.1; 536/23.1; 536/23.6

(58) Field of Classification Search
None
See application file for complete search history.

(56) References Cited

U.S. PATENT DOCUMENTS

| | | | |
|---|---|---|---|
| 2004/0255346 A1* | 12/2004 | Charng et al. | 800/278 |
| 2005/0108791 A1 | 5/2005 | Edgerton | |
| 2007/0016976 A1 | 1/2007 | Katagiri et al. | |

FOREIGN PATENT DOCUMENTS

| | | |
|---|---|---|
| WO | WO0073475 | 12/2000 |
| WO | WO0234925 | 5/2002 |
| WO | WO2004053055 | 6/2004 |
| WO | WO2006069201 | 6/2006 |
| WO | WO2006130156 | 12/2006 |

OTHER PUBLICATIONS

Wunderlich et al ((The Plant Journal, (2003) 35, 442-451).*
Schöffl et al. Model plants and Crop Improvements, Chapter 10: Identification of Heat Shock Factor Regulated Genes, 2007, pp. 228-242.*
Yuan Li et al (Bot. Bull. Acad. Sin. (2003) 44:129-140).*
Prändl et al (Mol Gen Genet (1998) 258: 269-278).*
Zhu et al Plant Mol Biol (2009) 71:451-467.*
Miller et al (Annals of Botany 98: 279-288, 2006).*
Ogawa et al., "High-level Overexpression of the *Arabidopsis* HsfA2 Gene Confers Not Only Increased Thermotolerance But Also Salt/Osmotic Stress Tolerance and Enhanced Callus Growth," J. Exp. Botany 58(12) 3373-3383, 2007.
Prandl et al., "HSF3, A New Heat Shock Factor From *Arabidopsis thaliana*, Derepresses the Heat Shock Response and Confers Thermotolerance When Overexpressed in Transgenic Plants," Mol. Gen. Genet. 258:269-278, 1998.
Kotak et al., "Characterization of C-terminal Domains of *Arabidopsis* Heat Stress Transcription Factors (Hsfs) and Identification of a New Signature Combination of Plant Class a HSfs with . . . Intracellular Localization" The Plant Journal 39:98-112, 2004.
Lee et al., "Derepression of the Activity of Genetically Engineered Heat Shock Factor Causes Constitutive Synthesis of Heat Shock Proteins and Increased Thermotolerance in Transgenic *Arabidopsis*", The Plant Journal 8(4):603-612, 1995.
Nover et al., "*Arabidopsis* and the Heat Stress Transcription Factor World: How Many Heat Stress Stranscription Factors Do We Need?", Cell Stress & Chaperones 6(3):177-189, 2001.
Ogawa et al., "High-level Overexpression of the *Arabidopsis* HsfA2 Gene Confers Not Only Increased Thermotolerance But Also Salt/Osmotic Stress Tolerance and Enhanced Callus Growth" J. Exp. Botany 58(12):3373-3383, 2007.
Shoji et al., "Two Types of Heat Shock Factors in Cultured Tobacco Cells", Plant Cell Reports 19(4):414-420, 2000.

* cited by examiner

*Primary Examiner* — Brent T Page
*Assistant Examiner* — Lee A Visone
(74) *Attorney, Agent, or Firm* — Duane Morris LLP; Lee Crews

(57) ABSTRACT

The present invention relates to methods and uses for improving traits in plants which are important in the field of agriculture. In particular, the methods and uses of the invention use a plant Hsf to increase plant productivity, water use efficiency, drought or pathogen resistance.

11 Claims, 14 Drawing Sheets

```
gagagagtct ctgtctctgt aaaagatatt tgagcttgag aagaacagaa gaaacttcca    60
ggatcaatca atcgatcaac tttagtgaac taactcttga tttttcattc gaagttatgg   120
aatcggttcc cgaatccgta ccatcgccga actcgaatac accgtcaata ccaccgccgg   180
tgaactccgt accgcctttc ttgagtaaaa cctacgacat ggttgatgat ccgttgacca   240
atgaggtcgt ttcgtggagc agcgggaaca acagcttcgt cgtctggagt gccccggagt   300
tctcgaaggt gctcttgccc aagtatttca agcacaacaa cttctccagc ttcgtcagac   360
agttaaatac ttatgtaagc atcatttttt gtgttattgt caatttattt ttctagaaat   420
tgatcgtttt ttcgtggtac aatttgggga acatcgtgaa atgttgaagg gttctagtct   480
tagtgactag atccatggat gtgttggatt attttttaaag ccatatcaat ctgtctactc   540
atcaaaagat tccacagaac tttgcaggcg cactgtcaca tatgtctgaa gattgtttcc   600
tcaattgttt tctgccttgt agctctaaca aaacagaatg tctatcagtt gtctgaacat   660
tagctttgtt ttcatttgta tatttccgtc caggtacact tttttgataa actaagaact   720
attactttcc ttataacatg gtgattttgt gctacaccca agcatagtgt ggagaatttg   780
tttacttctc aaactttgct ataactagaa catataacta atctggtctg ttttctagtc   840
tacctgttta atgtttatac attttttgtac aattgcgcta tgttggcttt tcttcttccc   900
ctaaattcaa gcaacatcgt ttcagttctt caatttgaat ttcgatattt atgatagcct   960
ctctgtattc tgatgtccag ggtttcagaa aagttgatcc tgaccgatgg gaatttgcaa  1020
atgaaggatt tcttagaggc cgaaaacaac tactgaagag tattgtcagg agaaaacctt  1080
cgcatgtgca gcagaatcag caacaaactc aagttcagag ctcatctgtt ggtgcttgtg  1140
tcgaggtggg gaagtttgga atagaagaag aagtggaaag acttaagcgg gataagaatg  1200
ttcttatgca agaactcgtc aggttaaggc agcaacagca agctactgaa aaccaactgc  1260
agaatgtggg acagaaagtt caggtgatgg agcaaaggca acaacaaatg atgtcgtttt  1320
tagcaaaggc tgttcaaagt ccaggttttct taaaccagtt agtacaacag ataataatg   1380
atggcaacag acaaattcca ggaagcaaca aaaagaggag acttcctgta gatgagcagg  1440
agaatcgtgg tgacaatgtg gctaatggtc ttaaccgcca gattgttaga tatcagccgt  1500
cgataaacga agcagcacaa aatatgcttc gacagttctt aaatactagt acctcacctc  1560
ggtatgaatc agtttcaaac aatcctgaca gtttcctatt gggtgatgtt cccagttcta  1620
cctctgtaga caatgggaac ccttcaagta gagtttctgg agtaacattg gccgagtttt  1680
cacccaacac agttcagtca gcaacgaatc aagtacccga agcaagtttg gctcatcatc  1740
ctcaagctgg tctggttcag ccaaatatag gtcaaagtcc ggctcaagga gcagcacctg  1800
cagactcttg gagccctgaa tttgatttag ttggatgcga gacagatagt ggagagtgtt  1860
ttgatccaat aatggctgtt ttagatgagt cagaaggcga tgcaatttct cctgaaggtg  1920
agggcaagat gaatgagtta ctggagggag tccctaagct gcccggaatc aagatccat   1980
tctgggaaca gttcttttct gttgaactcc cagcgattgc agatacagac gatattctat  2040
caggatcagt ggagaataat gacttggtat tggaacaaga accaaacgag tggacccgta  2100
atgaacaaca aatgaagtat cttactgaac aaatgggact gctttcctca gaagcacaga  2160
ggaaataaag gtaagaacat cgttaagttc aaacatgttt ctctgcattg ttgtatatct  2220
tgagagttat caattgtctc tcacaatgta gattttcagg ggaggttgca aaaggagata  2280
tgaaggaacg aggaatatat cagatggtgt gtataccctt tacatttta cttaaatgaa   2340
```

Figure 1

```
aaaaaaacag agagaagaaa cataaaagat ttaccaccaa gcttgtgaat agttagtaga   2400
gatcggtttt tgtgttgttt atattatact tttgtgtgaa aacgttcatc ttgttcaatt   2460
atcatctcac tagtacggta a                                            2481
```

Figure 1 (Continued)

PLANT RESPONSES

This application is a U.S. national phase application under 35 U.S.C. §371 of international application No. PCT/GB2008/050186, filed Mar. 17, 2008, which claims the benefit of GB Application No. 0704984.4, filed Mar. 15, 2007.

SEQUENCE LISTING

The instant application contains a Sequence Listing which has been submitted in ASCII format via EFS-Web and is hereby incorporated by reference in its entirety. The submitted ASCII copy was created on Jan. 7, 2010, modified on Sep. 25, 2011, and is 3,516 bytes in size.

FIELD OF THE INVENTION

The present invention relates to methods and uses for improving traits in plants which are important in the field of agriculture. In particular, the methods and uses of the invention can be employed to increase plant productivity, for example by improving the way in which plants make use of the water resources available to them or by conferring pathogen resistance.

BACKGROUND OF THE INVENTION

External conditions that adversely affect growth, development or productivity trigger a wide range of plant responses, such as altered gene expression, cellular metabolism and changes in growth rates and crop yields. There are two types of stress: biotic stress is imposed by other organisms, such as a pathogen, whereas abiotic stress arises from an excess or deficit in the physical or chemical environment, such as drought, salinity, high or low temperature or high light. Biotic and abiotic stresses can reduce average plant productivity by 65% to 87%, depending on the crop.

An example of biotic stress is pathogen infection. Plants have evolved defensive mechanisms, such as the induction of the expression of specific resistance genes upon infection. It is known that resistance is heritable and plant breeders have been breeding varieties of crop plants with disease resistance ever since. However, pests and pathogens have also developed ways to compromise plant resistance. Pathogens are adaptive by their ability to evolve strains that defeat the resistance genes deployed in crop plants by plant breeders. This has led to the need of continually updating and replacing varieties with different genes or combinations of genes for resistance in response to the ever-changing pathogen populations. Therefore, new ways of improving pathogen resistance are needed (Crute et al 1998, Cook et al 1996).

In addition to pathogen infection, plants are exposed to varying environmental conditions. One important factor in the development of plants and thus in agriculture is the availability of water. Water is essential for crop production because plants require water for growth and tissue expansion. Thus, the supply of fresh water is essential for all forms of agriculture, although the amount of water required varies greatly between different agricultural types and climatic regions.

There has been limited success with conventional breeding to improve the way in which plants use the water resources available. Genetic engineering is therefore considered an alternative. Several genes that regulate drought response have been identified in the model plant Arabidopsis. These are categorised as responsive to dehydration and early response to dehydration genes (Valliyodan et al 2006). One of the factors identified in regulating cold and drought stress responsive gene expression in Arabidopsis is a family of transcription factors termed DREB, which interact with a dehydration responsive element. Overexpression of DREB results in significant drought tolerance under water limited conditions. However, resistance to drought often compromises development of these transgenic plants under normal conditions. It has been shown that overexpression of DREB1/CBF and DREB2A driven by the CaMV 35S promoter causes growth retardation under normal conditions (Valliyodan et al 2006, Sakuma et al 2006, Qiang et al 2000). Thus, there has so far been no success in genetically modifying plants so that they show improved and more efficient use of water under normal non-drought conditions as well as under water deficit conditions.

Although increasing drought tolerance is desirable in the face of global warming, from an agricultural point of view, drought resistance is usually linked to low productivity, and is thus of limited use in agricultural production. Also, severe water deficits are generally rare in viable agriculture. Therefore, reducing the amount of water used per unit yield is now seen as the most promising way forward.

This is increasingly important due to the rising amounts of water which are used in agriculture and the changing climate. Globally, some $2.7 \times 10^3$ km$^3$ of water were used in agriculture in 2000. It is estimated that the production of 1 kg of wheat requires 1 m$^3$ of water, and 1 kg of rice requires at least 1.2 m$^3$ of water. In the 15 countries of the EU in 2003, an area equivalent to 15.5% of the arable and permanent crop area was irrigated, and irrigation comprised over half of the total water consumption (EEA 2003). Even within the humid, temperate climate of England, 147 kha of outdoor crops were irrigated in 2001 (about 3% of the cropped area), using $131 \times 10^6$ m$^3$ of water (Morison et al 2008; Rijsberman. 2004; Richards 2004; Food and Agriculture Organisation (FAO) 2003; Parry et al 2005.)

Thus, how to reduce agricultural water use and make water resources more sustainable is an increasingly urgent question. There is a need to develop crops that require less water to produce sufficient yield under normal conditions in addition to showing improved drought resistance. The amount of yield produced per unit water used is referred to as 'water productivity', a well known term in agriculture (Morison et al., 2008).

All eukaryotic organisms respond to an increase in the ambient temperature with the expression of a group of proteins known as heat shock proteins (HSPs). Key factors in the regulation of the expression of Hsp genes are the heat shock transcription factors (Hsfs) that act by binding to a highly conserved palindromic heat shock response sequence in the promoters of the target genes. In addition to mediating the response to heat stress, Hsfs are thought to be involved in cellular responses to oxidative stress, heavy metals and other stress responses (Panchuk et al 2002, Panikulangara et al 2004).

It is known that the basic structure of Hsfs and of their promoter recognition site is conserved throughout the eukaryotic kingdom (Kotak et al 2004, Miller and Mittler 2006). Hsfs have a modular structure with a highly conserved N-terminal DNA binding and a C-terminal activation domain. Other conserved domains include an oligomerisation domain, a nuclear localisation sequence and a nuclear export sequence. Thus, Hsfs are easily recognised by their conserved motifs essential for their function as transcription factors (Kotak et al 2004, Miller and Mittler 2006, Nover et al 2001).

Yeast and Drosophila contain only one Hsf gene, while vertebrates are thought to have three Hsf genes. In plants, Hsf genes have been identified in many species, for example maize, the model plant *Arabidopsis thaliana* (21 Hsfs), soybean (34 Hsfs), rice (23 Hsfs), barley, potato, tomato (18 Hsfs) and others. Hsfs within the plant kingdom are highly conserved and divided into three classes (A, B and C). For example, it has been found that a class of Hsfs in *Arabidopsis* is closely related to Hsf from rice and to Hsfs identified from ESTs in barley, potato, tomato and soy bean (Nover et al 2001 and Kotak et al 2004).

The invention is aimed at solving or at least mitigating the problems discussed above by introducing and expressing a gene sequence encoding a plant heat shock transcription factor.

SUMMARY OF THE INVENTION

The invention relates to methods and uses for improving a plant's tolerance to abiotic or biotic stress, not including heat stress. The method comprises introducing and overexpressing a polynucleotide sequence comprising or consisting of a plant Hsf into said plant. In particular, the invention provides methods and uses for improving traits in plants which are important in the field of agriculture selected from the group comprising improved productivity, preferably growth or yield, water use efficiency, water productivity, drought tolerance or pathogen resistance.

In one aspect, the invention provides a method for improving plant productivity comprising introducing and overexpressing a polynucleotide sequence comprising or consisting of a plant Hsf into said plant.

The invention also provides a method for improving water use efficiency in plants comprising introducing and overexpressing a polynucleotide sequence comprising or consisting of a plant Hsf into said plant.

Furthermore, there is provided a method for conferring pathogen resistance in plants comprising introducing and overexpressing a polynucleotide sequence comprising or consisting of a plant Hsf into said plant.

The invention also relates to uses of a plant Hsf in improving plant productivity, plant water use efficiency, water productivity, drought tolerance or pathogen resistance. In one embodiment, plant water use efficiency and water productivity are improved under normal, non drought conditions.

DETAILED DESCRIPTION

The present invention will now be further described. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

The practice of the present invention will employ, unless otherwise indicated, conventional techniques of botany, microbiology, tissue culture, molecular biology, chemistry, biochemistry and recombinant DNA technology, which are within the skill of the art. Such techniques are explained fully in the literature.

In a first aspect, the invention relates to a method for improving plant productivity comprising introducing and overexpressing a polynucleotide sequence comprising or consisting of a plant Hsf in said plant.

Plant productivity can be assessed by measuring plant growth or plant yield. Preferably, the term is used to describe an improvement in yield. This can be assessed by measuring seed yield, such as increased seed biomass or increased number of seeds. It can be improved by increasing water productivity.

According to the different aspects and embodiments of the invention, the plant into which a plant Hsf of plant origin is introduced may be any monocot or dicot plant.

A dicot plant may be selected from the families including, but not limited to Asteraceae, Brassicaceae (eg *Brassica napus*), Chenopodiaceae, Cucurbitaceae, Leguminosae (Caesalpiniaceae, Aesalpiniaceae Mimosaceae, Papilionaceae or Fabaceae), Maivaceae, Rosaceae or Solanaceae. For example, the plant may be selected from lettuce, sunflower, *Arabidopsis*, broccoli, spinach, water melon, squash, cabbage, tomato, potato, capsicum, tobacco, cotton, okra, apple, rose, strawberry, alfalfa, bean, soybean, field (fava) bean, pea, lentil, peanut, chickpea, apricots, pears, peach, grape vine or citrus species. In one embodiment, the plant is oilseed rape.

Also included are biofuel and bioenergy crops such as rape/canola, linseed, lupin and willow, poplar, poplar hybrids, Miscanthus or gymnosperms, such as loblolly pine. Also included are crops for silage (maize), grazing or fodder (grasses, clover, sanfoin, alfalfa), fibres (e.g. cotton, flax), building materials (e.g. pine, oak), pulping (e.g. poplar), feeder stocks for the chemical industry (e.g. high erucic acid oil seed rape, linseed) and for amenity purposes (e.g. turf grasses for golf courses), ornamentals for public and private gardens (e.g. snapdragon, petunia, roses, geranium, *Nicotiana* sp.) and plants and cut flowers for the home (African violets, Begonias, chrysanthemums, geraniums, Coleus spider plants, Dracaena, rubber plant).

A monocot plant may, for example, be selected from the families Arecaceae, Amaryllidaceae or Poaceae. For example, the plant may be a cereal crop, such as wheat, rice, barley, maize, oat sorghum, rye, onion, leek, millet, buckwheat, turf grass, Italian rye grass, sugarcane or *Festuca* species.

Preferably, the plant into which a plant Hsf is introduced is a crop plant. By crop plant is meant any plant which is grown on a commercial scale for human or animal consumption or use.

Preferred plants are maize, wheat, rice, oilseed rape, sorghum, soybean, potato, tomato, barley, pea, bean, field bean, lettuce, broccoli or other vegetable brassicas or poplar.

The polynucleotide according to the different aspects and embodiments of the invention comprises or consists of a plant heat shock transcription factor gene, i.e. a plant Hsf. The term plant heat shock transcription factor gene or plant Hsf refers to a nucleic acid sequence which encodes a plant heat shock transcription factor. The Hsf gene can be from genomic DNA and therefore contain introns, a cDNA copy synthesised from the Hsf3 mRNA or could be a completely synthetic copy of the coding sequence made by assembly of chemically synthesised oligonucleotides. The plant heat shock transcription factor gene sequence can be isolated from a plant and inserted into a vector/expression cassette for transformation, for example by using an artificial plant chromosome.

Within the scope of the invention is also a derivative of a Hsf gene, such as a mutant/mutated gene, chimeric gene or gene shuffled variant. For example, the mutant gene may be modified so that the resulting protein is constitutively active and cannot be inhibited by other components of the Hsf signalling pathway. The derivative gene expressed a protein which is biologically active. It may have 80% or more sequence homology with the wild type gene. Thus, the methods and uses of the invention also relates to methods and uses employing a Hsf derivative.

The Hsf polynucleotide is a transgene that is introduced in the plant. This can be carried out by various methods as known in the field of plant genetic engineering, for example using transformation with *Agrobacterium* or particle bombardment.

The plant heat shock transcription factor gene may be an exogenous gene, such as one or more *Arabidopsis* Hsf, overexpressed in a different plant species. Alternatively, the plant Hsf may be an endogenous plant Hsf, i.e. a plant Hsf that is endogenous to the plant in which it is introduced and overexpressed.

In one embodiment of the different aspects of the invention, the exogenous plant Hsf may originate from any plant, for example a family or species listed above and expressed in a different plant species according to the invention. There is a structural high similarity between Hsfs in the plant kingdom. Plant Hsfs are conserved throughout the plant kingdom and can be identified due to their conserved domains. Plant Hsfs are divided into three groups A, B and C. Thus, according to the invention, the plant Hsf may be selected from group A, B or C. For example, the plant Hsf may be an *Arabidopsis* Hsf, a tomato Hsf, such as LpHsfA1, LpHsfA2, LpHsfA3 or LpHsfB1. Alternatively, the plant Hsf may be derived from rice, wheat, pea, maize, tobacco or any crop cereal. Non limiting examples of known Hsfs which can be used according to the invention are given in tables 1 and 2.

| OsHsfA1a | AK100430 Os03g0854500 |
|---|---|
| OsHsfA2c | AK072391 Os10g0419300 |
| OsHsfA2b | AK101824 Os07g0178600 |
| OsHsfA2a | AK069579 ABF98829 |
| OsHsfA1a2d | AK066844 Os03g0161900 |
| OsHsfA2e | AK068660 Os03g0795900 |
| OsHsfA3 | AK101934 XM_466050 |
| OsHsfA4b | AK109856 Os01g0749300 |
| OsHsfA4d | AK100412 Os05g0530400 |
| OsHsfA5 | AK065643 Os02g0496100 |
| OsHsfA7 | AK064271 Os01g0571300 |
| OsHsfA9 | AK064271 Os03g0224700 |
| OsHsfB1 | AK101182 Os09g0456800 |
| OsHsfB2a | Os04g0568700 |
| OsHsfB2b | AK101700 Os08g0546800 |
| OsHsfB2c | AK106525 Os09g0526600 |
| OsHsfB4a | P0461F06.21 |
| OsHsfB4b | AK063952 Os07g0640900 |
| OsHsfB4c | Os09g0455200 |
| OsHsfB4d | AK069479 ABF96133 |
| OsHsfC1a | AK066316 Os01g0625300 |
| OsHsfC1b | AK106488 Os01g0733200 |
| OsHsfC2a | Os02g0232000 |
| OsHsfC2b | Os06g0553100 |

*Arabidopsis thaliana*

| AtHsfA1a | AT4G17750 |
|---|---|
| AtHsfA1b | AT5G16820 |
| AtHsfA1d | AT1G32330 |
| AtHsfA1e | AT3G02990 |
| AtHsfA2 | AT2G26150 |
| AtHsfA3 | AT5G03720 |
| AtHsfA4a | AT4G18880 |
| AtHsfA4c | AT5G45710 |
| AtHsfA5 | AT4G13980 |
| AtHsfA6a | AT5G43840 |
| AtHsfA6b | AT3G22830 |
| AtHsfA7a | AT3G51910 |
| AtHsfA7b | AT3G63350 |
| AtHsfA8 | AT1G67970 |
| AtHsfA9 | AT5G54070 |
| AtHsfB1 | AT4G36990 |
| AtHsfB2a | AT5G62020 |
| AtHsfB2b | AT4G11660 |
| AtHsfB3 | AT2G41690 |
| AtHsfB4 | AT1G46264 |
| AtHsfC1 | AT3G24520 |

Tomato
*Lycopersicon esculentum*

| LpHsfA1 | X67600 |
|---|---|
| LpHsfA2 | X67601 |
| LpHsfA3 | AF208544 |
| LpHsfB1 | X55347 |

Homology searches of plant sequence databases such as the expressed sequence tag (EST) cDNA databases using the HSF3 derived amino acid sequence readily detects many highly significant homologies corresponding to HSFs in the query species. In the examples below the amino acid sequence of HSF3 was used to query the following databases with a significance value (E) of less than $1e^{-10}$. The values and hits, including the identification number are all shown in table 2 below.

TABLE 2

| Soybean | | |
|---|---|---|
| gb\|AW569256.1\| si64g09.y1 Gm-r1030 *Glycine max* cDNA clone | 290 | 4e-78 |
| gb\|AW569138.1\| si63g09.y1 Gm-r1030 *Glycine max* cDNA clone | 287 | 2e-77 |
| gb\|BM086093.1\| sah35d07.y1 Gm-c1036 *Glycine max* cDNA clone | 238, | 1e-62 |
| gb\|CA938396.1\| sav31h12.y1 Gm-c1048 *Glycine max* cDNA clone | 213 | 5e-55 |
| gb\|BM521654.1\| sak60e12.y1 Gm-c1036 *Glycine max* cDNA clone | 211 | 2e-54 |
| gb\|BM527729.1\| sal65b05.y1 Gm-c1061 *Glycine max* cDNA clone | 209 | 5e-54 |
| gb\|AW395668.1\| sg73g10.y1 Gm-c1007 *Glycine max* cDNA clone | 201 | 2e-51 |
| gb\|CA801396.1\| sau05b03.y2 Gm-c1062 *Glycine max* cDNA clone | 195 | 1e-49 |
| gb\|AW508573.1\| si33f01.y1 Gm-r1030 *Glycine max* cDNA clone | 190 | 4e-48 |
| gb\|BI786160.1\| sai33f04.y1 Gm-c1065 *Glycine max* cDNA clone | 189 | 6e-48 |
| gb\|AW164509.1\| se74f12.y1 Gm-c1023 *Glycine max* cDNA clone | 166 | 7e-41 |
| gb\|BI471764.1\| sae83d02.y3 Gm-c1065 *Glycine max* cDNA clone | 162 | 1e-39 |
| gb\|BE611683.1\| sq86g05.y1 Gm-c1049 *Glycine max* cDNA clone | 160 | 4e-39 |
| gb\|AW132703.1\| se09a08.y1 Gm-c1013 *Glycine max* cDNA clone | 159 | 6e-39 |
| gb\|BE347442.1\| sp38d02.y1 Gm-c1043 *Glycine max* cDNA clone | 151 | 2e-36 |
| gb\|AW203851.1\| sf38h11.y1 Gm-c1028 *Glycine max* cDNA clone | 149 | 9e-36 |
| gb\|BG839442.1\|Gm01_17a10_A, Gm01_AAFC_ECORC_Glycine_max_cold_ | 147 | 2e-35 |
| gb\|BG352891.1\| sab92f08.y1 Gm-c1040 *Glycine max* cDNA clone | 146 | 6e-35 |
| gb\|BG789771.1\| sae55c03.y1 Gm-c1051 *Glycine max* cDNA clone | 142 | 1e-33 |
| gb\|AW596493.1\| sj13a09.y1 Gm-c1032 *Glycine max* cDNA clone | 141 | 2e-33 |
| gb\|BM523618.1\| sam86d01.y2 Gm-c1087 *Glycine max* cDNA clone | 139 | 7e-33 |
| gb\|BM188104.1\| saj84g05.y1 Gm-c1074 *Glycine max* cDNA clone | 139 | 7e-33 |
| gb\|BM094717.1\| saj19h06.y1 Gm-c1066 *Glycine max* cDNA clone | 139 | 7e-33 |
| gb\|AI900223.1\| sc02f05.y1 Gm-c1012 *Glycine max* cDNA clone | 139 | 7e-33 |

TABLE 2-continued

| | | |
|---|---|---|
| gb\|BM732569.1\| sa178h07.y1 Gm-c1061 *Glycine max* cDNA clone | 136 | 6e−32 |
| gb\|BI498205.1\| sag17c01.y1 Gm-c1080 *Glycine max* cDNA clone | 136 | 6e−32 |
| gb\|BU764266.1\| sas54g03.y1 Gm-c1023 *Glycine max* cDNA clone | 134 | 3e−31 |
| gb\|BQ094759.1\| san51d12.y1 Gm-c1052 *Glycine max* cDNA clone | 134 | 3e−31 |
| gb\|BI894096.1\| sai60a12.y1 Gm-c1068 *Glycine max* cDNA clone | 134 | 3e−31 |
| gb\|AW703969.1\| sk14g08.y1 Gm-c1023 *Glycine max* cDNA clone | 134 | 4e−31 |
| gb\|BM527450.1\| sa162a04.y1 Gm-c1061 *Glycine max* cDNA clone | 133 | 6e−31 |
| gb\|BG405291.1\| sac50e11.y1 Gm-c1062 *Glycine max* cDNA clone | 133 | 6e−31 |
| gb\|BG840046.1\|, Gm01__08b12__F, Gm01__AAFC__ECORC__Glycine__max__cold__ . . . | 132 | 1e−30 |
| gb\|CA936104.1\| sav05g11.y1 Gm-c1048 *Glycine max* cDNA clone | 130 | 3e−30 |
| gb\|BE346810.1\| sp31e01.y1 Gm-c1042 *Glycine max* cDNA clone | 130 | 3e−30 |
| gb\|BQ094171.1\| san43b07.y1 Gm-c1052 *Glycine max* cDNA clone | 130 | 4e−30 |
| gb\|BE020791.1\| sm52h09.y1 Gm-c1028 *Glycine max* cDNA clone | 127 | 3e−29 |
| gb\|CA850642.1\| D04F08.seq cDNA Peking library 2, 4 day SCN3 | 126 | 6e−29 |
| gb\|BM886719.1\| sam29c06.y1 Gm-c1068 *Glycine max* cDNA clone | 126 | 6e−29 |
| gb\|BU577235.1\| sar67d03.y1 Gm-c1074 *Glycine max* cDNA clone | 126 | 8e−29 |
| gb\|BF071322.1\| st45a08.y1 Gm-c1067 *Glycine max* cDNA clone | 125 | 1e−28 |
| gb\|CX711571.1\| gmrtDrNS01__35-D__M13R__F05__037.s2 Water stressed . . . | 116 | 6e−26 |
| gb\|BQ474006.1\| sap25b06.y1 Gm-c1082 *Glycine max* cDNA clone | 115 | 1e−25 |
| gb\|CO984075.1\| GM89021A1G02.r1 Gm-r1089 *Glycine max* cDNA | 109 | 7e−24 |
| gb\|BE019974.1\| sm38b12.y1 Gm-c1028 *Glycine max* cDNA clone | 108 | 1e−23 |
| gb\|CX711887.1\| gmrtDrNS01__39-D__M13R__C04__028.s3 | 84.7 | 5e−22 |
| gb\|BF067962.1\| st79c06.y1 Gm-c1054 *Glycine max* cDNA clone | 103 | 5e−22 |
| gb\|BU548776.1\| GM880016B20F09 Gm-r1088 *Glycine max* cDNA | 103 | 7e−22 |
| gb\|CA953210.1\| sav53h02.y1 Gm-c1069 *Glycine max* cDNA clone | 102 | 9e−22 |
| gb\|CA801977.1\| sau28a12.y1 Gm-c1062 *Glycine max* cDNA clone | 100 | 3e−21 |
| gb\|AW756148.1\| sl16e07.y1 Gm-c1036 *Glycine max* cDNA clone | 99.4 | 1e−20 |
| gb\|CD403874.1\| Gm__ck26662 Soybean induced by Salicylic Acid G. | 90.9 | 4e−18 |
| gb\|BE330669.1\| so82h05.y1 Gm-c1040 *Glycine max* cDNA clone | 89.4 | 1e−17 |
| gb\|BI469342.1\| sai10f07.y1 Gm-c1053 *Glycine max* cDNA clone | 89.0 | 1e−17 |
| gb\|BM271159.1\| sak05h06.y1 Gm-c1074 *Glycine max* cDNA clone | 87.0 | 5e−17 |
| gb\|DY577402.1\| sgs2c.pk001.j19 DupontLib. *Glycine max* cDNA 5', m | 86.7 | 7e−17 |
| gb\|CX705290.1\| gmrtDrNS01__40-B__M13R__H02__002.s2 | 85.9 | 1e−16 |
| gb\|AW508846.1\| si41a12.y1 Gm-r1030 *Glycine max* cDNA clone GEN . . . | 85.1 | 2e−16 |
| gb\|BU578607.1\| sar59b05.y1 Gm-c1074 *Glycine max* cDNA clone | 82.8 | 1e−15 |
| gb\|BQ473641.1\| sap15g12.y1 Gm-c1082 *Glycine max* cDNA clone | 82.0 | 2e−15 |
| gb\|BE348040.1\| sp10e12.y1 Gm-c1042 *Glycine max* cDNA clone | 79.7 | 8e−15 |
| gb\|BF425514.1\| su56f05.y1 Gm-c1069 *Glycine max* cDNA clone | 79.3 | 1e−14 |
| gb\|BQ628408.1\| sap46f03.y1 Gm-c1087 *Glycine max* cDNA clone | 79.0 | 1e−14 |
| gb\|BM269600.1\| sak01h05.y1 Gm-c1074 *Glycine max* cDNA clone | 76.6 | 7e−14 |
| gb\|AW620962.1\| sj98b03.y1 Gm-c1023 *Glycine max* cDNA clone | 76.6 | 7e−14 |
| gb\|AW704152.1\| sk28b02.y1 Gm-c1028 *Glycine max* cDNA clone | 75.1 | 2e−13 |
| gb\|BI316569.1\| saf05a10.y1 Gm-c1065 *Glycine max* cDNA clone | 74.3 | 3e−13 |
| gb\|BU760760.1\| sas58b07.y1 Gm-c1023 *Glycine max* cDNA clone | 72.8 | 1e−12 |
| gb\|BE475593.1\| sp78e05.y1 Gm-c1044 *Glycine max* cDNA clone | 68.2 | 3e−11 |
| Barley | | |
| gb\|BI951809.1\| HVSMEm0003A03f *Hordeum vulgare* green seedling | 241 | 2e−63 |
| gb\|DN182018.1\| HO22J02S HO *Hordeum vulgare* cDNA clone HO22J02 . . . | 239 | 1e−62 |
| dbj\|AV833112.1\| AV833112 K. Sato unpublished cDNA library: | 235 | 2e−61 |
| dbj\|AV941967.1\| AV941967 K. Sato unpublished cDNA library | 201 | 2e−51 |
| gb\|BU967095.1\| HB03E12r BC *Hordeum vulgare* subsp. *vulgare* | 193 | 6e−49 |
| gb\|BU967280.1\| HB03N01r BC *Hordeum vulgare* subsp. *vulgare* | 190 | 7e−48 |
| gb\|CA002527.1\| HS07M12r HS *Hordeum vulgare* subsp. *vulgare* | 177 | 4e−44 |
| gb\|BQ466839.1\| HS01L22T HS *Hordeum vulgare* subsp. *vulgare* | 177 | 4e−44 |
| gb\|BM373839.2\| EBma03__SQ002__N22__R maternal, 8 DPA | 176 | 1e−43 |
| gb\|BQ466452.1\| HT02J04r HT *Hordeum vulgare* subsp. *vulgare* | 176 | 1e−43 |
| gb\|BQ762325.1\| EBro01__SQ005__B18 __R root, 3 week, | 175 | 2e−43 |
| gb\|BF628773.2\| HVSMEb0008B10f *Hordeum vulgare* seedling shoot | 164 | 5e−40 |
| gb\|BF264338.2\| HV__CEa0009C13f *Hordeum vulgare* seedling green | 159 | 1e−38 |
| gb\|DN183502.1\| HO17K20S HO *Hordeum vulgare* cDNA clone HO17K20 . . . | 156 | 8e−38 |
| gb\|BQ466741.1\| HS01H02T HS *Hordeum vulgare* subsp. *vulgare* | 154 | 3e−37 |
| gb\|DN156902.1\| GCN003J14u GCN *Hordeum vulgare* cDNA clone GCN0 . . . | 154 | 5e−37 |
| gb\|BQ660530.1\| HI04A10u HI *Hordeum vulgare* subsp. *vulgare* | 152 | 1e−36 |
| gb\|CB870232.1\| HC13L22w CH *Hordeum vulgare* cDNA clone HC13L22 . . . | 152 | 2e−36 |
| gb\|BE216310.2\| HV__CEb0010C13f *Hordeum vulgare* seedling green | 151 | 3e−36 |
| gb\|BQ740081.1\| HC04G06 HC *Hordeum vulgare* subsp. *vulgare* cDNA | 150 | 6e−36 |
| gb\|BI959876.1\| HVSMEn0022C22f *Hordeum vulgare* rachis EST | 146 | 8e−35 |
| gb\|BQ660415.1\| HI02G20u HI *Hordeum vulgare* subsp. *vulgare* | 143 | 7e−34 |
| gb\|CA019131.1\| HV10O05r HV *Hordeum vulgare* subsp. *vulgare* | 138 | 3e−32 |
| gb\|CA028721.1\| HZ63A24r HZ *Hordeum vulgare* subsp. *vulgare* | 137 | 4e−32 |
| gb\|BU969351.1\| HB11E12r BC *Hordeum vulgare* subsp. *vulgare* | 136 | 9e−32 |
| gb\|BF616419.2\| HVSMEc0007I04f *Hordeum vulgare* seedling shoot | 134 | 6e−31 |
| gb\|BI948455.1\| HVSMEI0009K13f *Hordeum vulgare* spike EST | 133 | 1e−30 |
| dbj\|BY838837.1\| BY838837 Etiolated seedling shoot *Hordeum* | 132 | 2e−30 |
| dbj\|BY847793.1\| BY847793 Seminal root *Hordeum vulgare* subsp. | 132 | 2e−30 |
| gb\|CA003800.1\| HS15J20r HS *Hordeum vulgare* subsp. *vulgare* | 132 | 2e−30 |
| gb\|CA001818.1\| HS05K18r HS *Hordeum vulgare* subsp. *vulgare* | 132 | 2e−30 |
| gb\|BM369160.2\| EBem07__SQ002__L22__R embryo, 28 DPA | 132 | 2e−30 |
| dbj\|BY853068.1\| BY853068 Germination shoots *Hordeum vulgare* | 129 | 2e−29 |

TABLE 2-continued

| | | |
|---|---|---|
| dbj\|BY847188.1\| BY847188 Seminal root *Hordeum vulgare* subsp. | 129 | 2e−29 |
| gb\|BF264951.3\| HV__CEa0010N10f *Hordeum vulgare* seedling green . . . | 128 | 3e−29 |
| gb\|BQ739839.1\| HB04B12 HB *Hordeum vulgare* subsp. *vulgare* cDNA. | 125 | 3e−28 |
| gb\|BQ758567.1\| EBma07__SQ002__K03__R maternal, 21 DPA | 124 | 6e−28 |
| dbj\|BY848814.1\| BY848814 Seminal root *Hordeum vulgare* subsp. | 121 | 4e−27 |
| gb\|DN183559.1\| HO17C03S HO *Hordeum vulgare* cDNA clone HO17C03 | 95.1 | 1e−26 |
| gb\|CV063030.1\| BNEL85h11 Barley EST endosperm library *Hordeum* | 119 | 1e−26 |
| gb\|CV059324.1\| BNEL46h12 Barley EST endosperm library *Hordeum*. | 119 | 1e−26 |
| gb\|CV055928.1\| BNEL12A4 Barley EST endosperm library *Hordeum* | 119 | 1e−26 |
| gb\|BM098554.2\| EBem08__SQ003__G12__R embryo, 40 DPA | 117 | 7e−26 |
| gb\|BM098700.2\| EBem08__SQ003__N07__R embryo, 40 DPA | 116 | 1e−25 |
| gb\|CB873818.1\| HC13L22y CH *Hordeum vulgare* cDNA clone HC13L22 | 115 | 2e−25 |
| gb\|BE602936.2\| HVSMEh0101B12f *Hordeum vulgare* 5-45 DAP spike | 115 | 3e−25 |
| dbj\|BY847001.1\| BY847001 Seminal root *Hordeum vulgare* subsp. | 93.2 | 6e−25 |
| gb\|CA001991.1\| HS06D04r HS *Hordeum vulgare* subsp. *vulgare* | 113 | 8e−25 |
| gb\|CA008447.1\| HU10P22r HU *Hordeum vulgare* subsp. *vulgare* | 112 | 1e−24 |
| gb\|CV057176.1\| BNEL24h11 Barley EST endosperm library *Hordeum*. | 111 | 3e−24 |
| gb\|BE216016.3\| HV__CEb0009C04f *Hordeum vulgare* seedling green | 77.8 | 9e−24 |
| dbj\|BY849120.1\| BY849120 Germination shoots *Hordeum vulgare* | 109 | 1e−23 |
| gb\|CV057937.1\| BNEL32e5 Barley EST endosperm library *Hordeum* | 107 | 6e−23 |
| gb\|BQ759041.1\| EBma07__SQ003__H17__R maternal, 21 DPA | 102 | 1e−21 |
| dbj\|BY849968.1\| BY849968 Germination shoots *Hordeum vulgare* | 102 | 2e−21 |
| gb\|BQ758691.1\| EBma07__SQ002__D17__R maternal, 21 DPA | 100 | 9e−21 |
| dbj\|BY850372.1\| BY850372 Germination shoots *Hordeum vulgare* | 90.9 | 6e−18 |
| gb\|BQ463252.1\| HI04I11r HI *Hordeum vulgare* subsp. *vulgare* | 90.5 | 7e−18 |
| dbj\|AV834862.1\| AV834862 K. Sato unpublished cDNA library: Ho . . . | 89.7 | 1e−17 |
| gb\|BU990279.1\| HF24J17r HF *Hordeum vulgare* subsp. *vulgare* cDNA | 88.6 | 3e−17 |
| dbj\|BY854029.1\| BY854029 Germination shoots *Hordeum vulgare* | 84.0 | 7e−16 |
| gb\|CA001926.1\| HS06A02r HS *Hordeum vulgare* subsp. *vulgare* cDNA | 84.0 | 7e−16 |
| gb\|BM815949.1\| HB108G05__SK.ab1 HB *Hordeum vulgare* subsp. | 84.0 | 7e−16 |
| gb\|BF619429.2\| HVSMEc0003F06f *Hordeum vulgare* seedling shoot | 84.0 | 7e−16 |
| gb\|BF630021.2\| HVSMEb0007L02f *Hordeum vulgare* seedling shoot | 84.0 | 7e−16 |
| gb\|BF265538.1\| HV__CEa0012I16f *Hordeum vulgare* seedling green | 82.0 | 3e−15 |
| dbj\|BJ477649.1\| BJ477649 K. Sato unpublished cDNA library | 77.0 | 8e−14 |
| dbj\|BJ469794.1\| BJ469794 K. Sato unpublished cDNA library | 68.9 | 2e−13 |
| gb\|BU997524.1\| HI08D24r HI *Hordeum vulgare* subsp. *vulgare* | 69.7 | 1e−11 |
| Maize | | |
| gb\|EE046500.1\| ZM__BFc0116004.r ZM__BFc *Zea mays* cDNA clone | 354 | 3e−97 |
| gb\|DR827048.1\| ZM__BFb0070B11.f ZM__BFb *Zea mays* cDNA 3', mRNA seq | 320 | 7e−87 |
| gb\|EE153197.1\| ZM__BFc0057D18.f ZM__BFc *Zea mays* cDNA clone | 301 | 4e−81 |
| gb\|EE176144.1\| ZM__BFc0155L14.f ZM__BFc *Zea mays* cDNA clone | 300 | 1e−80 |
| gb\|EE016215.1\| ZM__BFc0066O22.r ZM__BFc *Zea mays* cDNA clone | 283 | 1e−75 |
| gb\|DR814130.1\| ZM__BFb0043K05.r ZM__BFb *Zea mays* cDNA 5', mRNA seq | 251 | 3e−66 |
| gb\|EE044700.1\| ZM__BFc0113I19.r ZM__BFc *Zea mays* cDNA clone | 237 | 8e−62 |
| gb\|CO466103.1\| MZCCL20041E02.g Maize Endosperm cDNA Library | 228 | 3e−59 |
| gb\|CX129539.1\| QCD4f05.yg QCD *Zea mays* cDNA clone QCD4f05, mRNA | 223 | 2e−57 |
| gb\|EE020758.1\| ZM__BFc0074B16.r ZM__BFc *Zea mays* cDNA clone | 213 | 1e−54 |
| gb\|DR830042.1\| ZM__BFb0077D11.r ZM__BFb *Zea mays* cDNA 5', mRNA seq | 213 | 1e−54 |
| gb\|EE036952.1\| ZM__BFc0100H21.r ZM__BFc *Zea mays* cDNA clone | 205 | 3e−52 |
| gb\|EE174627.1\| ZM__BFc0153H07.r ZM__BFc *Zea mays* cDNA clone | 200 | 1e−50 |
| gb\|EE168641.1\| ZM__BFc0143L05.r ZM__BFc *Zea mays* cDNA clone | 200 | 1e−50 |
| gb\|EC878082.1\| ZM__BFc0012B11.r ZM__BFc *Zea mays* cDNA clone | 200 | 1e−50 |
| gb\|DV531708.1\| ZM__BFb0221P10.r ZM__BFb *Zea mays* cDNA 5', mRNA seq | 200 | 1e−50 |
| gb\|DR819313.1\| ZM__BFb0055J22.r ZM__BFb *Zea mays* cDNA 5', mRNA seq | 200 | 1e−50 |
| gb\|DR814313.1\| ZM__BFb0043O15.r ZM__BFb *Zea mays* cDNA 5', mRNA seq | 200 | 1e−50 |
| gb\|DV521145.1\| ZM__BFb0206F11.r ZM__BFb *Zea mays* cDNA 5', mRNA seq | 199 | 2e−50 |
| gb\|EE023205.1\| ZM__BFc0078F16.r ZM__BFc *Zea mays* cDNA clone | 197 | 5e−50 |
| gb\|DT644796.1\| ZM__BFb0104H15.r ZM__BFb *Zea mays* cDNA 5', mRNA seq | 197 | 5e−50 |
| gb\|EE045614.1\| ZM__BFc0115D04.r ZM__BFc *Zea mays* cDNA clone | 129 | 6e−50 |
| gb\|EE184383.1\| ZM__BFc0168M02.r ZM__BFc *Zea mays* cDNA clone | 197 | 7e−50 |
| gb\|EB676377.1\| ZM__BFb0340P21.r ZM__BFb *Zea mays* cDNA 5', mRNA seq | 197 | 9e−50 |
| gb\|EB641134.1\| ZM__BFb0330I04.r ZM__BFb *Zea mays* cDNA 5', mRNA seq | 197 | 9e−50 |
| gb\|DV514179.1\| ZM__BFb0196A08.r ZM__BFb *Zea mays* cDNA 5', mRNA seq | 197 | 9e−50 |
| gb\|DT938818.1\| ZM__BFb0120H03.r ZM__BFb *Zea mays* cDNA 5', mRNA seq | 197 | 9e−50 |
| gb\|EC878282.1\| ZM__BFc0012G03.r ZM__BFc *Zea mays* cDNA clone | 194 | 6e−49 |
| gb\|DR803312.1\| ZM__BFb0027O21.r ZM__BFb *Zea mays* cDNA 5', mRNA seq | 192 | 2e−48 |
| gb\|DV536183.1\| ZM__BFb0228J07.r ZM__BFb *Zea mays* cDNA 5', mRNA seq | 192 | 3e−48 |
| gb\|EE016587.1\| ZM__BFc0067H20.r ZM__BFc *Zea mays* cDNA clone | 110 | 1e−47 |
| gb\|EE037596.1\| ZM__BFc0101H15.r ZM__BFc *Zea mays* cDNA clone | 188 | 3e−47 |
| gb\|EE181056.1\| ZM__BFc0163K15.r ZM__BFc *Zea mays* cDNA clone | 186 | 2e−46 |
| gb\|EB821749.1\| ZM__BFb0383A18.r ZM__BFb *Zea mays* cDNA 5', mRNA seq | 184 | 5e−46 |
| gb\|DR972034.1\| ZM__BFb0095A05.r ZM__BFb *Zea mays* cDNA 5', mRNA seq | 182 | 3e−45 |
| gb\|EE046747.1\| ZM__BFc0119D19.r ZM__BFc *Zea mays* cDNA clone | 179 | 2e−44 |
| gb\|EC898631.1\| ZM__BFc0043J13.r ZM__BFc *Zea mays* cDNA clone | 100 | 2e−41 |
| gb\|EE016207.1\| ZM__BFc0066O16.r ZM__BFc *Zea mays* cDNA clone | 166 | 2e−40 |
| gb\|EE172761.1\| ZM__BFc0150H22.r ZM__BFc *Zea mays* cDNA clone | 97.1 | 3e−40 |
| gb\|EC893479.1\| ZM__BFc0035L05.r ZM__BFc *Zea mays* cDNA clone | 165 | 4e−40 |
| gb\|CA828716.1\| 1114032E05.y2 1114 - Unigene IV from Maize | 164 | 7e−40 |
| gb\|DY689425.1\| ZM__BFb0285C17.r ZM__BFb *Zea mays* cDNA 5', mRNA seq | 162 | 2e−39 |

TABLE 2-continued

| | | |
|---|---|---|
| gb\|DV538370.1\| ZM__BFb0231M05.r ZM__BFb Zea mays cDNA 5', mRNA seq | 162 | 2e−39 |
| gb\|DR965723.1\| ZM__BFb0085M05.r ZM__BFb Zea mays cDNA 5', mRNA seq | 162 | 2e−39 |
| gb\|DV167013.1\| ZM__BFb0164N15.r ZM__BFb Zea mays cDNA 5', mRNA seq | 161 | 4e−39 |
| gb\|DR820230.1\| ZM__BFb0058D10.r ZM__BFb Zea mays cDNA 5', mRNA seq | 161 | 4e−39 |
| gb\|BU079565.1\| 946145D05.y1 946 - tassel primordium prepared | 161 | 4e−39 |
| gb\|EE165047.1\| ZM__BFc0137E21.r ZM__BFc Zea mays cDNA clone | 161 | 6e−39 |
| gb\|EE037488.1\| ZM__BFc0101E17.r ZM__BFc Zea mays cDNA clone | 160 | 7e−39 |
| gb\|DV519877.1\| ZM__BFb0204H22.r ZM__BFb Zea mays cDNA 5', mRNA seq | 160 | 7e−39 |
| gb\|DV508968.1\| ZM__BFb0187M19.r ZM__BFb Zea mays cDNA 5', mRNA seq | 160 | 7e−39 |
| gb\|DV168574.1\| ZM__BFb0167E09.r ZM__BFb Zea mays cDNA 5', mRNA seq | 160 | 7e−39 |
| gb\|DV033268.1\| ZM__BFb0157G21.r ZM__BFb Zea mays cDNA 5', mRNA seq | 160 | 7e−39 |
| gb\|DV019914.1\| ZM__BFb0138A11.r ZM__BFb Zea mays cDNA 5', mRNA seq | 160 | 7e−39 |
| gb\|DT641438.1\| ZM__BFb0099I01.r ZM__BFb Zea mays cDNA 5', mRNA seq | 160 | 7e−39 |
| gb\|DR970291.1\| ZM__BFb0092H08.r ZM__BFb Zea mays cDNA 5', mRNA seq | 160 | 7e−39 |
| gb\|DR969885.1\| ZM__BFb0091N01.r ZM__BFb Zea mays cDNA 5', mRNA seq | 160 | 7e−39 |
| gb\|DR828268.1\| ZM__BFb0072L05.r ZM__BFb Zea mays cDNA 5', mRNA seq | 160 | 7e−39 |
| gb\|EE026988.1\| ZM__BFc0084J01.r ZM__BFc Zea mays cDNA clone ZM__ . . . | 160 | 9e−39 |
| gb\|DN560588.1\| ME24-A03-T3-96-R1 E7PCR Zea mays cDNA clone E7 . . . | 160 | 1e−38 |
| gb\|BM500210.1\| PAC000000000320 Pioneer AF-1 array Zea mays cDNA, | 160 | 1e−38 |
| gb\|DV032779.1\| ZM__BFb0156L04.r ZM__BFb Zea mays cDNA 5', mRNA seq | 159 | 2e−38 |
| gb\|DR828476.1\| ZM__BFb0073E20.r ZM__BFb Zea mays cDNA 5', mRNA seq | 159 | 2e−38 |
| gb\|CA830206.1\| 1117003H06.y1 1117 - Unigene V from Maize | 159 | 2e−38 |
| gb\|EC891458.1\| ZM__BFc0032K08.r ZM__BFc Zea mays cDNA clone | 158 | 4e−38 |
| gb\|EC879486.1\| ZM__BFc0014C20.r ZM__BFc Zea mays cDNA clone | 158 | 4e−38 |
| gb\|CO451095.1\| MZCCL10160C11.g Maize Endosperm cDNA Library | 90.1 | 7e−38 |
| gb\|BQ295716.1\| 1091041H03.y1 1091 | 157 | 8e−38 |
| gb\|CO525958.1\| 3530__1__172__1__F12.y__1 3530 - Full length cDNA | 154 | 7e−37 |
| gb\|CO466022.1\| MZCCL20042D10.g Maize Endosperm cDNA Library | 154 | 9e−37 |
| gb\|DY240393.1\| ZM__BFb0259N07.r ZM__BFb Zea mays cDNA 5', mRNA seq | 153 | 1e−36 |
| gb\|EE044234.1\| ZM__BFc0112N15.r ZM__BFc Zea mays cDNA clone | 152 | 3e−36 |
| gb\|EE020950.1\| ZM__BFc0074H05.r ZM__BFc Zea mays cDNA clone | 150 | 1e−35 |
| gb\|DR807887.1\| ZM__BFb0034F24.r ZM__BFb Zea mays cDNA 5', mRNA seq | 150 | 1e−35 |
| gb\|CF002965.1\| QBH17e07.xg QBH Zea mays cDNA clone QBH17e07, mRN | 147 | 6e−35 |
| gb\|EC886519.1\| ZM__BFc0025E04.r ZM__BFc Zea mays cDNA clone | 147 | 1e−34 |
| gb\|CO518740.1\| 3530__1__122__1__E05.y__1 3530 - Full length cDNA | 146 | 1e−34 |
| gb\|CF244820.1\| 3530__1__5__1__A07.y__2 3530 - Full length cDNA | 146 | 1e−34 |
| gb\|EE015293.1\| ZM__BFc0064K18.r ZM__BFc Zea mays cDNA clone | 144 | 7e−34 |
| gb\|CF629555.1\| zmrws48__0A20-002-g05.s0 zmrws48 Zea mays cDNA 3', | 140 | 8e−33 |
| gb\|CD443521.1\| EL01N0427E10.b Endosperm__4 Zea mays cDNA, mRNA se | 140 | 8e−33 |
| gb\|EE013968.1\| ZM__BFc0062H12.r ZM__BFc Zea mays cDNA clone | 140 | 1e−32 |
| gb\|EE013967.1\| ZM__BFc0062H12.f ZM__BFc Zea mays cDNA clone | 140 | 1e−32 |
| gb\|DR967139.1\| ZM__BFb0087N19.r ZM__BFb Zea mays cDNA 5', mRNA seq | 140 | 1e−32 |
| gb\|AW065936.1\| 687003D06.y1 687 | 140 | 1e−32 |
| gb\|BQ295608.1\| 1091038B11.y1 1091 | 140 | 1e−32 |
| gb\|EC880371.1\| ZM__BFc0015I01.r ZM__BFc Zea mays cDNA clone | 139 | 3e−32 |
| gb\|DY688753.1\| ZM__BFb0284B21.r ZM__BFb Zea mays cDNA 5', mRNA seq | 139 | 3e−32 |
| gb\|DY624757.1\| ZM__BFb0347H01.r ZM__BFb Zea mays cDNA 5', mRNA seq | 139 | 3e−32 |
| gb\|DV539151.1\| ZM__BFb0232N24.r ZM__BFb Zea mays cDNA 5', mRNA seq | 139 | 3e−32 |
| gb\|DV537032.1\| ZM__BFb0229M13.r ZM__BFb Zea mays cDNA 5', mRNA seq | 139 | 3e−32 |
| gb\|DV535973.1\| ZM__BFb0228E13.r ZM__BFb Zea mays cDNA 5', mRNA seq | 139 | 3e−32 |
| gb\|DV535514.1\| ZM__BFb0227J20.r ZM__BFb Zea mays cDNA 5', mRNA seq | 139 | 3e−32 |
| gb\|DV530458.1\| ZM__BFb0220E01.r ZM__BFb Zea mays cDNA 5', mRNA seq | 139 | 3e−32 |
| gb\|DV515662.1\| ZM__BFb0198F14.r ZM__BFb Zea mays cDNA5', mRNA seq | 139 | 3e−32 |
| gb\|DV507107.1\| ZM__BFb0185C03.r ZM__BFb Zea mays cDNA 5', mRNA seq | 139 | 3e−32 |
| gb\|DV025493.1\| ZM__BFb0146B22.r ZM__BFb Zea mays cDNA 5', mRNA seq | 139 | 3e−32 |
| gb\|DV025290.1\| ZM__BFb0145N07.r ZM__BFb Zea mays cDNA 5', mRNA seq | 139 | 3e−32 |
| gb\|DT946133.1\| ZM__BFb0133K13.r ZM__BFb Zea mays cDNA 5', mRNA seq | 139 | 3e−32 |
| gb\|DT645771.1\| ZM__BFb0105P04.r ZM__BFb Zea mays cDNA 5', mRNA seq | 139 | 3e−32 |
| Wheat | | |
| gb\|DR735777.1\| FGAS081411 Triticum aestivum | 319 | 2e−86 |
| dbj\|CJ649060.1\| CJ649060 Y. Ogihara unpublished cDNA library | 238 | 4e−62 |
| gb\|DR740109.1\| FGAS085037 Triticum aestivum FGAS: Library | 197 | 9e−50 |
| gb\|CD881399.1\| F1.103B17F010329 F1 Triticum aestivum cDNA | 194 | 6e−49 |
| dbj\|CJ655373.1\| CJ655373 Y. Ogihara unpublished cDNA library | 189 | 2e−47 |
| gb\|CD884036.1\| F1.115E10F010507 F1 Triticum aestivum cDNA | 186 | 2e−46 |
| gb\|CV762533.1\| FGAS056922 Triticum aestivum FGAS: Library 2 | 185 | 5e−46 |
| gb\|DR740033.1\| FGAS084961 Triticum aestivum FGAS: Library 2 | 184 | 6e−46 |
| gb\|BI479783.1\| WHE3452__A08__A16ZS Wheat pre-anthesis spike cDNA. | 175 | 5e−43 |
| gb\|CD919573.1\| G608.113N06F010911 G608 Triticum aestivum cDNA | 164 | 7e−40 |
| gb\|CD939626.1\| OV.114E09F010312 OV Triticum aestivum cDNA | 162 | 4e−39 |
| emb\|AL812570.1\| AL812570 e: 310 Triticum aestivum cDNA clone | 157 | 1e−37 |
| gb\|CD871372.1\| AZO2.118B14F010207 AZO2 Triticum aestivum cDNA . . . | 157 | 1e−37 |
| gb\|CD909725.1\| G468.113G04F010820 G468 Triticum aestivum cDNA | 154 | 7e−37 |
| dbj\|BJ304701.1\| BJ304701 Y. Ogihara unpublished cDNA library | 152 | 3e−36 |
| gb\|CV766170.1\| FGAS060557 Triticum aestivum FGAS: Library 2 | 152 | 3e−36 |
| gb\|BE488911.1\| WHE1077__G04__N07ZS Wheat unstressed seedling | 152 | 4e−36 |
| gb\|BE418746.1\| SCL074.E11R990812 ITEC SCL Wheat Leaf Library | 151 | 8e−36 |
| gb\|CD868305.1\| AZO2.108I04F001113 AZO2 Triticum aestivum cDNA. | 148 | 5e−35 |
| gb\|CD918044.1\| G608.107M05F010905 G608 Triticum aestivum cDNA. | 147 | 1e−34 |

TABLE 2-continued

| | | |
|---|---|---|
| gb\|CA733194.1\| wlp1c.pk007.b24 wlp1c *Triticum aestivum* cDNA | 147 | 1e-34 |
| gb\|CK208279.1\| FGAS019979 *Triticum aestivum* FGAS: Library 5 | 146 | 2e-34 |
| dbj\|CJ627951.1\| CJ627951 Y. Ogihara unpublished cDNA library | 145 | 4e-34 |
| gb\|CK213161.1\| FGAS025066 *Triticum aestivum* FGAS: Library 6 | 143 | 2e-33 |
| gb\|CV781279.1\| FGAS075690 *Triticum aestivum* FGAS: Library 2 | 137 | 9e-32 |
| gb\|CK196713.1\| FGAS005173 *Triticum aestivum* FGAS: Library 3 | 137 | 1e-31 |
| gb\|CD894087.1\| G118.125F14F010828 G118 *Triticum aestivum* cDNA | 137 | 1e-31 |
| gb\|CA741191.1\| wia1c.pk001.g8 wia1c *Triticum aestivum* cDNA | 137 | 1e-31 |
| gb\|BQ240791.1\| TaE05012H01R TaE05 *Triticum aestivum* cDNA | 137 | 1e-31 |
| gb\|BU100082.1\| WHE3314_H10_O20ZS Chinese Spring wheat drought | 137 | 1e-31 |
| emb\|AJ601747.1\| AJ601747 T05 *Triticum aestivum* cDNA clone | 135 | 3e-31 |
| gb\|BU100475.1\| WHE3353_G05_N09ZS Chinese Spring aluminum-stre . . . | 135 | 3e-31 |
| gb\|BE426590.1\| WHE0336_F08_L16ZS Wheat unstressed seedling | 135 | 4e-31 |
| gb\|CD924507.1\| G750.113E16F010706 G750 *Triticum aestivum* cDNA | 135 | 6e-31 |
| gb\|BF200512.1\| WHE0825-0828_B15_B15ZS | 134 | 1e-30 |
| gb\|CV762050.1\| FGAS056439 *Triticum aestivum* FGAS: Library | 132 | 4e-30 |
| gb\|CD868306.1\| AZO2.108I04R010328 AZO2 *Triticum aestivum* cDNA | 132 | 4e-30 |
| gb\|CD924855.1\| G750.114O18F010706 G750 *Triticum aestivum* cDNA | 131 | 6e-30 |
| gb\|BE471094.1\| WHE0284_H12_O24ZS | 130 | 1e-29 |
| gb\|CV780245.1\| FGAS074654 *Triticum aestivum* FGAS: Library 2 | 128 | 5e-29 |
| emb\|AJ602329.1\| AJ602329 T05 *Triticum aestivum* cDNA clone | 127 | 9e-29 |
| gb\|CV768109.1\| FGAS062500 *Triticum aestivum* FGAS: Library 2 | 127 | 2e-28 |
| gb\|CD881419.1\| F1.103C19F010328 F1 *Triticum aestivum* cDNA | 125 | 3e-28 |
| gb\|CD920551.1\| G608.117J13F010912 G608 *Triticum aestivum* cDNA | 125 | 4e-28 |
| dbj\|CJ660695.1\| CJ660695 Y. Ogihara unpublished cDNA library | 123 | 2e-27 |
| dbj\|CJ696176.1\| CJ696176 Y. Ogihara unpublished cDNA library | 122 | 3e-27 |
| gb\|DR736601.1\| FGAS081971 *Triticum aestivum* FGAS: Library 5 | 120 | 2e-26 |
| dbj\|CJ627959.1\| CJ627959 Y. Ogihara unpublished cDNA library | 119 | 2e-26 |
| dbj\|CJ501729.1\| CJ501729 Y. Ogihara unpublished cDNA library | 118 | 5e-26 |
| gb\|CV780793.1\| FGAS075204 *Triticum aestivum* FGAS: Library 2 | 118 | 7e-26 |
| gb\|CA701457.1\| wkm2c.pk006.e15 wkm2c *Triticum aestivum* cDNA | 105 | 8e-26 |
| gb\|CV775774.1\| FGAS070178 *Triticum aestivum* FGAS: Library 2 | 102 | 3e-25 |
| gb\|CD919574.1\| G608.113N06R011027 G608 *Triticum aestivum* cDNA. | 115 | 4e-25 |
| gb\|BE499216.1\| WHE0972_H11_O22ZS Wheat pre-anthesis spike cDNA . . . | 112 | 4e-24 |
| gb\|CK216192.1\| FGAS028177 *Triticum aestivum* FGAS: Library 6 | 110 | 1e-23 |
| gb\|CA632168.1\| wle1n.pk0062.f9 wle1n *Triticum aestivum* cDNA | 110 | 1e-23 |
| emb\|AL816629.1\| AL816629 I: 226 *Triticum aestivum* cDNA clone | 67.4 | 4e-23 |
| gb\|CV758782.1\| FGAS053164 *Triticum aestivum* FGAS: Library 2 | 107 | 1e-22 |
| gb\|BE406522.1\| WHE0417_f11_k21zB | 106 | 3e-22 |
| gb\|CA732800.1\| wlp1c.pk004.j3 wlp1c *Triticum aestivum* cDNA | 103 | 2e-21 |
| gb\|CA697753.1\| wlk4.pk0010.g3 wlk4 *Triticum aestivum* cDNA | 61.6 | 5e-21 |
| gb\|CD882214.1\| F1.105L19F010330 F1 *Triticum aestivum* cDNA | 101 | 7e-21 |
| gb\|CA657309.1\| wlm0.pk0034.e2 wlm0 *Triticum aestivum* cDNA | 97.8 | 1e-19 |
| dbj\|CJ712793.1\| CJ712793 Y. Ogihara unpublished cDNA library | 93.6 | 2e-18 |
| dbj\|CJ519157.1\| CJ519157 Y. Ogihara unpublished cDNA library | 92.0 | 5e-18 |
| dbj\|CJ712794.1\| CJ712794 Y. Ogihara unpublished cDNA library | 91.7 | 7e-18 |
| gb\|CD918480.1\| G608.109J07F010907 G608 *Triticum aestivum* cDNA | 91.7 | 7e-18 |
| gb\|BQ839307.1\| WHE4164_F06_K12ZS Wheat CS whole plant cDNA | 90.1 | 2e-17 |
| emb\|AL818825.1\| AL818825 I: 125 *Triticum aestivum* cDNA clone | 87.0 | 2e-16 |
| gb\|BF202987.1\| WHE1768_A07_A14ZS Wheat pre-anthesis spike cDNA . . . | 84.7 | 9e-16 |
| gb\|CD925960.1\| G750.119H10F010711 G750 *Triticum aestivum* cDNA . . . | 84.0 | 1e-15 |
| dbj\|CJ608117.1\| CJ608117 Y. Ogihara unpublished cDNA library | 82.4 | 4e-15 |
| emb\|AJ602330.1\| AJ602330 T05 *Triticum aestivum* cDNA clone E08 . . . | 82.4 | 4e-15 |
| gb\|CK211694.1\| FGAS023548 *Triticum aestivum* FGAS: Library 6 | 81.6 | 7e-15 |
| gb\|BE470775.1\| WHE0281_A11_B22ZS | 81.6 | 7e-15 |
| gb\|CA610399.1\| wr1.pk0119.f3 wr1 *Triticum aestivum* cDNA | 65.9 | 9e-15 |
| gb\|DY741996.1\| EST0565 Cold treated wheat cDNA library | 81.3 | 1e-14 |
| gb\|CA596291.1\| wpa1c.pk012.m23 wpa1c *Triticum aestivum* cDNA | 81.3 | 1e-14 |
| gb\|BE427506.1\| PSR7104 ITEC PSR Wheat Pericarp/Testa | 76.6 | 1e-14 |
| dbj\|CJ640745.1\| CJ640745 Y. Ogihara unpublished cDNA library | 77.8 | 1e-13 |
| gb\|CA620714.1\| wl1n.pk0067.b9 wl1n *Triticum aestivum* cDNA | 75.9 | 4e-13 |
| emb\|AJ603615.1\| AJ603615 T07 *Triticum aestivum* cDNA clone | 75.5 | 5e-13 |
| dbj\|BJ232988.1\| BJ232988 Y. Ogihara unpublished cDNA library | 72.4 | 4e-12 |
| gb\|CA645001.1\| wre1n.pk0086.b5 wre1n *Triticum aestivum* cDNA | 71.2 | 1e-11 |
| gb\|CA484478.1\| WHE4307_A11_B21ZS Wheat meiotic anther cDNA | 67.0 | 2e-10 |
| Potato | | |
| gb\|CK253280.1\| EST736917 potato callus cDNA library, normaliz . . . | 324 | 2e-88 |
| gb\|CK267715.1\| EST713793 potato abiotic stress cDNA library S . . . | 323 | 3e-88 |
| gb\|CK246340.1\| EST729977 potato callus cDNA library, normaliz . . . | 308 | 1e-83 |
| gb\|CK244536.1\| EST728173 potato callus cDNA library, normaliz . . . | 306 | 6e-83 |
| gb\|BG890899.1\| EST516750 cSTD *Solanum tuberosum* cDNA clone cS . . . | 304 | 2e-82 |
| gb\|CK246138.1\| EST729775 potato callus cDNA library, normaliz . . . | 303 | 3e-82 |
| gb\|CK245930.1\| EST729567 potato callus cDNA library, normaliz . . . | 295 | 2e-80 |
| gb\|CK277468.1\| EST723546 potato abiotic stress cDNA library S . . . | 292 | 7e-79 |
| gb\|CK253321.1\| EST736958 potato callus cDNA library, normaliz . . . | 246 | 2e-76 |
| gb\|CK251625.1\| EST735262 potato callus cDNA library, normaliz . . . | 267 | 3e-71 |
| gb\|CK251428.1\| EST735065 potato callus cDNA library, normaliz . . . | 263 | 5e-70 |
| gb\|BQ510589.2\| EST618004 Generation of a set of potato cDNA c . . . | 243 | 5e-64 |
| gb\|DN922927.1\| 44403.2 Common Scab-Challenged Tubers *Solanum* . . . | 219 | 8e-57 |

TABLE 2-continued

| | | |
|---|---|---|
| gb\|BG599468.1\| EST504363 cSTS *Solanum tuberosum* cDNA clone cS . . . | 214 | 3e−55 |
| gb\|CK269104.1\| EST715182 potato abiotic stress cDNA library S . . . | 212 | 1e−54 |
| gb\|CK262462.1\| EST708540 potato abiotic stress cDNA library S . . . | 212 | 1e−54 |
| gb\|CK252508.1\| EST736145 potato callus cDNA library, normaliz . . . | 212 | 1e−54 |
| gb\|CK245866.1\| EST729503 potato callus cDNA library, normaliz . . . | 212 | 1e−54 |
| gb\|CV429240.1\| 51723.1 After-Cooking Darkening C *Solanum tube* . . . | 211 | 2e−54 |
| gb\|BG890138.1\| EST515989 cSTD *Solanum tuberosum* cDNA clone cS . . . | 211 | 2e−54 |
| gb\|CV431358.1\| 55572.1 After-Cooking Darkening C *Solanum tube* . . . | 209 | 1e−53 |
| gb\|BF459947.1\| 068G10 Mature tuber lambda ZAP *Solanum tuberos* . . . | 205 | 1e−52 |
| gb\|CK264318.1\| EST710396 potato abiotic stress cDNA library S . . . | 204 | 3e−52 |
| gb\|BG594178.1\| EST492856 cSTS *Solanum tuberosum* cDNA clone cS . . . | 203 | 4e−52 |
| gb\|BI406849.1\| 182A06 Mature tuber lambda ZAP *Solanum tuberos* . . . | 201 | 2e−51 |
| gb\|BG595575.1\| EST494253 cSTS *Solanum tuberosum* cDNA clone cS . . . | 200 | 5e−51 |
| gb\|CK719979.1\| 20306 Swollen Stolon *Solanum tuberosum* cDNA, mRNA | 198 | 1e−50 |
| gb\|BG886998.1\| EST512849 cSTD *Solanum tuberosum* cDNA clone cS . . . | 198 | 1e−50 |
| gb\|BG890352.1\| EST516203 cSTD *Solanum tuberosum* cDNA clone cS . . . | 195 | 2e−49 |
| gb\|CN213018.1\| 26561 Suspension culture *Solanum tuberosum* cDNA, | 194 | 3e−49 |
| gb\|EG012052.1\| STDB004A01u STDB *Solanum tuberosum* cDNA clone . . . | 194 | 4e−49 |
| gb\|BG596222.1\| EST494900 cSTS *Solanum tuberosum* cDNA clone cS . . . | 168 | 5e−49 |
| gb\|CV474156.1\| 22487.1 Developing Tubers *Solanum tuberosum* cD . . . | 192 | 1e−48 |
| gb\|BI176643.1\| EST517588 cSTE *Solanum tuberosum* cDNA clone cS . . . | 190 | 4e−48 |
| gb\|BG890868.1\| EST516719 cSTD *Solanum tuberosum* cDNA clone cS . . . | 190 | 5e−48 |
| gb\|BE922055.1\| EST425824 potato leaves and petioles *Solanum t* . . . | 189 | 9e−48 |
| gb\|DN923069.1\| 44928.2 Common Scab-Challenged Tubers *Solanum* . . . | 188 | 1e−47 |
| gb\|BG887370.1\| EST513221 cSTD *Solanum tuberosum* cDNA clone cS . . . | 187 | 4e−47 |
| gb\|BG351853.1\| 135A04 Mature tuber lambda ZAP *Solanum tuberos* . . . | 186 | 7e−47 |
| gb\|BG591987.1\| EST499829 *P. infestans*-challenged leaf *Solanum* . . . | 180 | 4e−45 |
| gb\|BG889138.1\| EST514989 cSTD *Solanum tuberosum* cDNA clone cS . . . | 180 | 5e−45 |
| gb\|CK277133.1\| EST723211 potato abiotic stress cDNA library S . . . | 179 | 9e−45 |
| gb\|CK269720.1\| EST715798 potato abiotic stress cDNA library S . . . | 179 | 9e−45 |
| gb\|CK851489.1\| 11654 Stolon *Solanum tuberosum* cDNA, mRNA sequenc | 119 | 1e−44 |
| gb\|CN216247.1\| 30125 Suspension culture *Solanum tuberosum* cDNA, | 178 | 2e−44 |
| gb\|CK256967.1\| EST740604 potato callus cDNA library, normaliz . . . | 178 | 2e−44 |
| gb\|CK255235.1\| EST738872 potato callus cDNA library, normaliz . . . | 178 | 2e−44 |
| gb\|CK249408.1\| EST733045 potato callus cDNA library, normaliz . . . | 178 | 2e−44 |
| gb\|CK261460.1\| EST707538 potato abiotic stress cDNA library S . . . | 177 | 4e−44 |
| gb\|BQ121678.2\| EST607254 mixed potato tissues *Solanum tuberos* . . . | 176 | 6e−44 |
| gb\|BG886969.1\| EST512820 cSTD *Solanum tuberosum* cDNA clone cS . . . | 175 | 2e−43 |
| gb\|BG888694.1\| EST514545 cSTD *Solanum tuberosum* cDNA clone cS . . . | 172 | 1e−42 |
| gb\|BF459641.1\| 062F02 Mature tuber lambda ZAP *Solanum tuberos* . . . | 172 | 1e−42 |
| gb\|BF153546.1\| 028C10 Mature tuber lambda ZAP *Solanum tuberos* . . . | 172 | 1e−42 |
| gb\|BG597894.1\| EST496572 cSTS *Solanum tuberosum* cDNA clone cS . . . | 171 | 3e−42 |
| gb\|BG595042.1\| EST493720 cSTS *Solanum tuberosum* cDNA clone cS . . . | 169 | 7e−42 |
| gb\|CV430232.1\| 53385.1 After-Cooking Darkening C *Solanum tube* . . . | 169 | 9e−42 |
| gb\|BG890527.1\| EST516378 cSTD *Solanum tuberosum* cDNA clone cS . . . | 168 | 2e−41 |
| gb\|CV471720.1\| 44928.1 Common Scab-Challenged Tubers *Solanum* . . . | 167 | 4e−41 |
| gb\|BQ116126.2\| EST601702 mixed potato tissues *Solanum tuberos* . . . | 97.4 | 1e−40 |
| gb\|BQ511608.2\| EST619023 Generation of a set of potato cDNA c . . . | 163 | 5e−40 |
| gb\|CV496124.1\| 73841.1 Cold Sweetening B *Solanum tuberosum* cD . . . | 163 | 7e−40 |
| gb\|CK720145.1\| 20511 Swollen Stolon *Solanum tuberosum* cDNA, mRNA | 162 | 1e−39 |
| gb\|BI176663.1\| EST517608 cSTE *Solanum tuberosum* cDNA clone cS . . . | 161 | 2e−39 |
| gb\|BG888216.1\| EST514067 cSTD *Solanum tuberosum* cDNA clone cS . . . | 160 | 3e−39 |
| gb\|CK250720.1\| EST734357 potato callus cDNA library, normaliz . . . | 160 | 4e−39 |
| gb\|BG886541.1\| EST512392 cSTD *Solanum tuberosum* cDNA clone cS . . . | 160 | 6e−39 |
| gb\|CV471787.1\| 45004.1 Common Scab-Challenged Tubers *Solanum* . . . | 159 | 7e−39 |
| gb\|BI405991.1\| 150C03 Mature tuber lambda ZAP *Solanum tuberos* . . . | 159 | 1e−38 |
| gb\|DV623092.1\| 92505.1 Cold Sweetening C *Solanum tuberosum* cD . . . | 155 | 1e−37 |
| gb\|BE342382.1\| EST395226 potato stolon, Cornell University So . . . | 152 | 2e−36 |
| gb\|BI178192.1\| EST519137 cSTE *Solanum tuberosum* cDNA clone cS . . . | 151 | 2e−36 |
| gb\|BQ509197.2\| EST616612 Generation of a set of potato cDNA c . . . | 150 | 3e−36 |
| gb\|AW906822.1\| EST342945 potato stolon, Cornell University So . . . | 150 | 4e−36 |
| gb\|DN941337.1\| 55572.2 After-Cooking Darkening C *Solanum tube* . . . | 150 | 6e−36 |
| gb\|CN216727.1\| 30658 Suspension culture *Solanum tuberosum* cDNA, | 149 | 1e−35 |
| gb\|CK261481.1\| EST707559 potato abiotic stress cDNA library S . . . | 146 | 6e−35 |
| gb\|BQ510562.2\| EST617977 Generation of a set of potato cDNA c . . . | 146 | 8e−35 |
| gb\|CK851608.1\| 11803 Stolon *Solanum tuberosum* cDNA, mRNA sequenc | 145 | 1e−34 |
| gb\|BQ505416.2\| EST612831 Generation of a set of potato cDNA c . . . | 145 | 1e−34 |
| gb\|BG593665.1\| EST492343 cSTS *Solanum tuberosum* cDNA done cS . . . | 145 | 1e−34 |
| gb\|DN909107.1\| 57843.2 Developing Tubers *Solanum tuberosum* cD . . . | 145 | 2e−34 |
| gb\|DN907365.1\| 22487.2 Developing Tubers *Solanum tuberosum* cD . . . | 145 | 3e−34 |
| gb\|CV477893.1\| 57843.1 Developing Tubers *Solanum tuberosum* cD . . . | 145 | 2e−34 |
| gb\|CK274767.1\| EST720845 potato abiotic stress cDNA library S . . . | 143 | 5e−34 |
| gb\|CK258841.1\| EST742478 potato callus cDNA library, normaliz . . . | 143 | 5e−34 |
| gb\|CK258748.1\| EST742385 potato callus cDNA library, normaliz . . . | 143 | 7e−34 |
| gb\|BE920995.1\| EST424764 potato leaves and petioles *Solanum t* . . . | 142 | 9e−34 |
| gb\|DN923089.1\| 45004.2 Common Scab-Challenged Tubers *Solanum* . . . | 142 | 1e−33 |
| gb\|BF187134.1\| EST443421 potato stolon, Cornell University So . . . | 141 | 3e−33 |
| gb\|BF187133.1\| EST443420 potato stolon, Cornell University So . . . | 141 | 3e−33 |
| gb\|CK263459.1\| EST709537 potato abiotic stress cDNA library S . . . | 140 | 4e−33 |
| gb\|AW906840.1\| EST342963 potato stolon, Cornell University So . . . | 139 | 1e−32 |

TABLE 2-continued

| | | |
|---|---|---|
| gb\|CK256905.1\| EST740542 potato callus cDNA library, normaliz . . . | 139 | 1e−32 |
| gb\|CV434757.1\| 58247.1 Suspension culture *Solanum tuberosum* c . . . | 137 | 3e−32 |
| gb\|CK278836.1\| EST724914 potato abiotic stress cDNA library S . . . | 137 | 3e−32 |
| gb\|BF052865.1\| EST438095 potato leaves and petioles *Solanum t* . . . | 137 | 3e−32 |
| gb\|BE471540.1\| EST416393 potato stolon, Cornell University So . . . | 134 | 3e−31 |
| gb\|DV625610.1\| 95977.1 Cold Sweetening C *Solanum tuberosum* cD . . . | 132 | 1e−30 |
| gb\|DN849475.1\| 13215.2 Stolon *Solanum tuberosum* cDNA clone 13 . . . | 132 | 1e−30 |

In one embodiment of the different aspects of the invention, an *Arabidopsis* Hsf selected from the *Arabidopsis* Hsf listed above, is overexpressed in another plant. The *Arabidopsis* Hsf is selected from the group comprising AtHsfA1a, AtHsfA1b, AtHsfA1d, AtHsfA1e, AtHsfA2, AtHsfA3, AtHsfA4a, AtHsfA4c, AtHsfA5, AtHsfA6a, AtHsfA6b, AtHsfA7a, AtHsfA7b, AtHsfA8, AtHsfA9, AtHsfB1, AtHsfB2a, AtHsfB2b, AtHsfB3, AtHsfB4 or AtHsfC1. In one embodiment, the *Arabidopsis* Hsf is AtHSFA1b. The full sequence of AtHSFA1b is shown in FIG. 1 (SEQ No 1).

The plant in which the Hsf is overexpressed may be any plant as listed herein. Preferably, the *Arabidopsis* Hsf, for example AtHSFA1b is overexpressed in a crop, for example a cereal, such as wheat, rice, barley, maize, oat sorghum, rye, onion, leek, millet, buckwheat, turf grass, Italian rye grass, sugarcane or *Festuca* species. However, the applicability of the invention is not limited to the sequence shown in Seq ID No 1 as a skilled person would understand that other Hsfs isolated or derived from *Arabidopsis* or from other plants can also be used. Any combination of a plant Hsf for example as listed herein, in another plant, for example as listed herein, is within the scope of the invention.

In another embodiment of the different aspects of the invention, an endogenous plant Hsf may be overexpressed according to the methods and uses of the invention. For example, a tomato Hsf may be overexpressed in tomato, a wheat Hsf may be expressed in wheat, a rice Hsf may be overexpressed in rice. Plants and their one or more Hsf may be selected from any plant, such as from one of the families or species listed above.

Overexpression according to the invention means that the transgene is expressed at a level that is higher than expression driven by its endogenous promoter. For example, overexpression may be carried out using a strong promoter, such as the cauliflower mosaic virus promoter (CaMV35S), the rice actin promoter or the maize ubiquitin promoter or any promoter that gives enhanced expression. Alternatively, enhanced or increased expression can be achieved by using transcription or translation enhancers or activators and may incorporate enhancers into the gene to further increase expression. Furthermore, an inducible expression system may be used, such as a steroid or ethanol inducible expression system. The coding sequence may be on a monocistronic or polycistronic messenger RNA. Also envisaged is ectopic expression, i.e. gene expression in a tissue in which it is normally not expressed According to the different aspects of the invention, plant characteristics are increased or improved. This is understood to mean an increase or improvement in plant productivity, water use efficiency, water productivity, drought tolerance or pathogen resistance compared to the level as found in a wild type plant.

According to one embodiment of the first aspect of the invention, the method increases water productivity. Thus, the method can be used to increase water productivity.

As used herein, water productivity describes the amount of yield produced per unit of water (for example ml or l) used. The transgenic plants as described herein require a lower amount of water than a wild type plant to produce the same amount of yield under normal non drought conditions where water is not at a shortage. Thus, according to the invention, water productivity can be improved under non drought conditions. For example, water productivity can be improved under non drought conditions by expression of the *Arabidopsis* Hsf is AtHSFA1b in another plant as defined herein.

In a different embodiment of first aspect of the invention, the method improves plant productivity under water deficit conditions. Thus, the method of the first aspect confers plant drought tolerance.

Water deficit or water limited conditions as used herein refer to conditions where water is at a shortage. This includes conditions where water is at a shortage compared to the normal average of water available to a plant grown in the particular environment, for example due to a change in climate or unseasonable weather. It also refers to conditions where water is generally known to be scarce, for example in arid climatic zones. Water shortage for a prolonged period of time is known as drought.

In another embodiment of the method of the first aspect of the invention, the method of the invention confers pathogen resistance. Plants with ability to resist infection by a particular pathogen are referred to as having increased resistance to that pathogen. Pathogens according to the different aspects of the invention include any viral, bacterial, fungi or animal pathogens, such as nematodes or insects, which infect plants. In one embodiment, the pathogen may be *Pseudomonas syringae* pv. Tomato, turnip crinkle virus or *Hyaloperonospora parasitica*. Fungal pathogens according to the invention include, but are not limited to the rust fungi (order Uridenales) e.g. *Puccinia graminis, Puccinia striiformis* (yellow rust) *P. recondite* and other *Puccinia* species, flax rust (*Melampsora lini*); *Rhizoctonia* sp. or *Phakospora pachyrhizi* (Soybean rust), the powdery mildew fungi (order Erysiphales, e.g barley powdery mildew (*Blumeria graminis*); *Erisyphe* sp. (infects legumes, trees and shrubs), *Leveillula* sp. (infects Solanaceae), *Golovinomyces* sp. (infect Cucurbits and Compositae), *Podosphaera* sp. (infects Rosaceae); *Fusarium* sp. *Verticillium* sp., Rice blast fungus *Magnoporthe grisea* or Potato blight (*Phytophtora infestans*).

Bacterial pathogens according to the invention include, but are not limited to *Pseudomonas syringae* (various pathovars), *Xanthomonas* sp. (e.g. *X. campestris* infects Brassicas, *X. axonopodis* causes citrus canker).

Viral pathogens according to the invention include, but are not limited to Tobacco mosaic virus (Solanaceae), tomato spotted wilt virus, rice tungrovirus, maize rough dwarf virus. Maize streak virus, cucumber mosaic virus, potato viruses X and Y, brome mosaic virus, pepper mild mottle virus, pea seed borne mosaic virus or pea ennation virus.

In a second aspect, the invention relates to a method for improving water use efficiency in plants comprising introducing and over-expressing a polynucleotide sequence comprising or consisting of a plant Hsf into said plant. In particular, water use efficiency can be improved under non drought conditions. For example, water use efficiency can be improved under non drought conditions by expression of the *Arabidopsis* Hsf is AtHSFA1 b in another plant as defined herein.

The term water use efficiency as used herein relates to the plants ability of using a water supply efficiently under normal or water deficit conditions. Because the plants according to the invention use water more efficiently than a wild type plant, they show drought resistance and thus prolonged lifespan under water limiting conditions. However, the inventors have also surprisingly found that the plants according to the invention use water more efficiently under normal non-drought conditions compared to wild type plants. As shown in the examples, plants according to the invention require less amount of water than wild type plants to survive and produce yield, thus they use the water supply more efficiently. It will be appreciated that the term normal conditions refers to conditions which are not exceptional, i.e. conditions in which water is not limited. Drought conditions are not normal conditions as water is at a deficit. It will also be appreciated that what in detail is to be understood by normal conditions depends on the plant concerned and on the climatic zone in which the plant is grown.

Thus, in one embodiment of the second aspect of the invention, the method increases water productivity. The method as described in the second aspect of the invention can thus be used to increase water productivity.

In another embodiment, the method improves water use efficiency under water deficit conditions. Therefore, the method increases plant drought tolerance. As shown in examples 2 to 7, plants transformed with a gene sequence encoding a plant HSF polypeptide whose expression is regulated by a strong promoter have improved resistance to prolonged periods of water shortage, i.e. drought conditions. Wild type plant survival rates are very low under these conditions whereas the transgenic plants survive and produce yield.

In another aspect, the invention relates to a method for increasing water productivity. Water productivity can be increased under normal conditions, i.e. conditions where water is not limited. In a further aspect, the invention provides a method for conferring drought resistance In a further aspect of the invention, the invention relates to the use of a polynucleotide sequence comprising or consisting of a plant Hsf in improving plant productivity.

Another aspect of the invention relates to the use of a polynucleotide sequence comprising or consisting of a plant Hsf in improving water use efficiency. In particular, this use relates to improving water use efficiency under normal non drought conditions or under drought conditions. Therefore, according to the invention, a plant Hsf can be used to improve water productivity, thereby enabling the plant to use less water than a wild type plant. Thus, the amount of water used in irrigation of crop plants can be reduced. In addition, the use according to the invention also provides that a plant Hsf can be used to improve water use efficiency under water deficit conditions, such as drought conditions.

The invention also provides the use of a polynucleotide sequence comprising or consisting of a plant Hsf in improving water productivity and the use in conferring drought tolerance.

In a final aspect, the invention provides the use of a polynucleotide sequence comprising or consisting of a plant Hsf in conferring pathogen resistance. The pathogen may be selected from those described herein.

The invention is further described by reference to the non-limiting figures and examples.

FIGURES

FIG. 1 shows SEQ ID No 1, the full length genomic sequence of AtHSFA1b.

Figure 4:

FIG. 4 shows plants which were not watered for 2.5 weeks and then rewatered. The picture was taken 48 hours after rewatering. Transgenic plants are marked with an arrow.

Figure 5A:
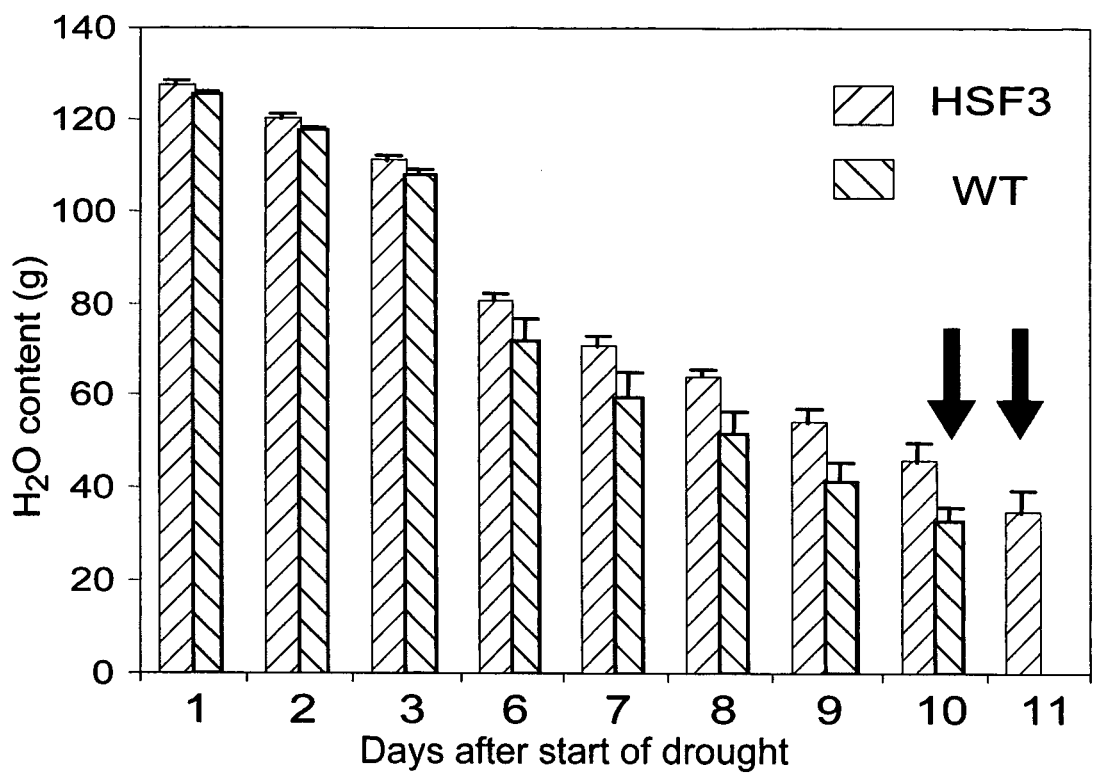

FIG. 5a shows a decline in pot water content for 35S-Hsf3 (HSF3) and wild type (WT) plants under drought conditions in a glasshouse. Withdrawal of water began at day 0. Re-watering commenced when the pot water content had attained 33 g (indicated by the arrows). Note that this took 24 hours longer for 35S-Hsf3 plants.

Figure 5B:
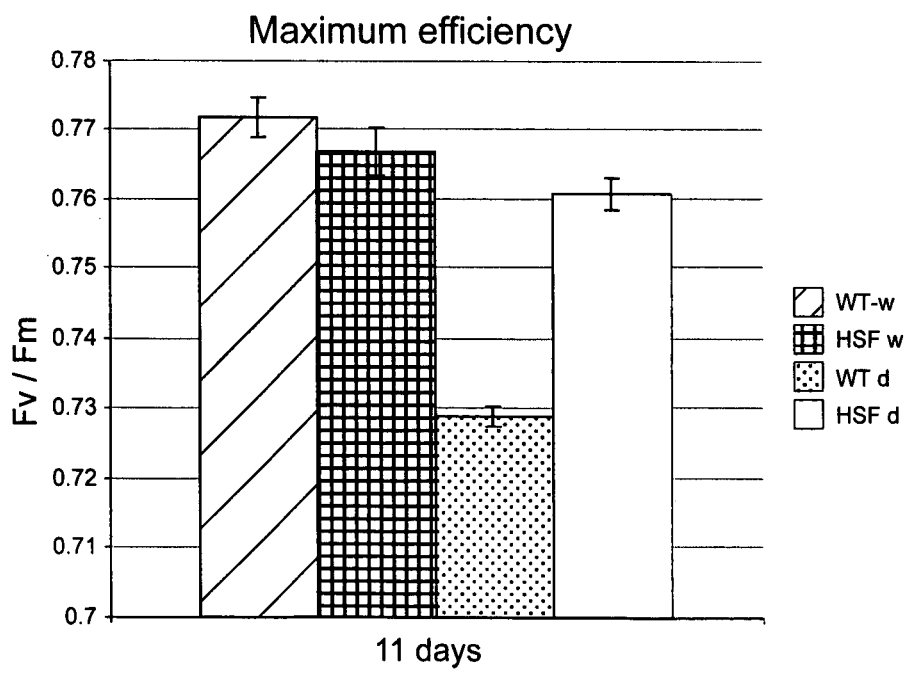

FIG. 5b shows the quantum efficiency of photosynthetic electron transport (Fv/Fm) in 35S-Hsf3 versus wild type plants in watered conditions (WT-w and HSF w) and just prior to recommencing watering as indicated (WT d and HSF d).

Figure 6:
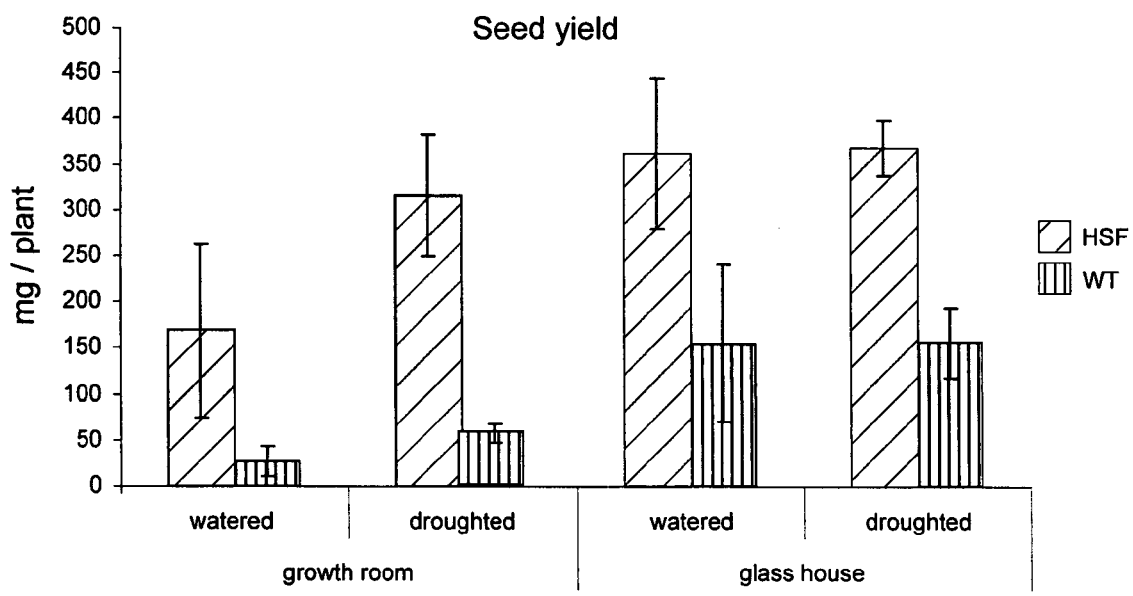

FIG. 6 shows the total seed yield after 10-11 days of drought and then subsequent re-watering until seed set. Under well-watered conditions, in both sets of conditions, 35S-Hsf3 plants yield better than WT. This differential is maintained after a moderate drought stress.

Figure 7:
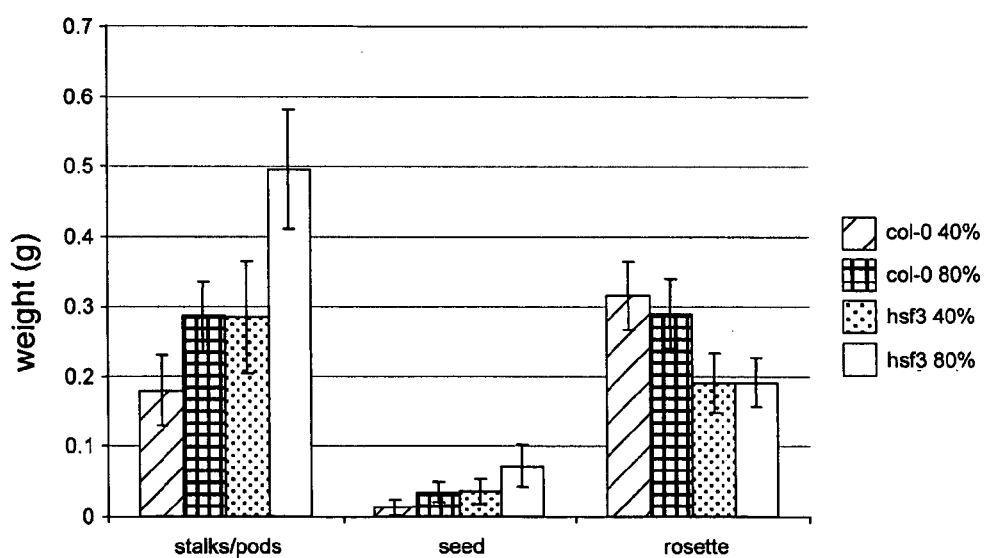

FIG. 7 shows the vegetative and reproductive biomass as well as seed yield of plants kept at different soil water contents (40% and 80%). In both soil water contents Hsf3 plants show higher seed yield and reproductive biomass, but reduced vegetative biomass.

Figure 8A:
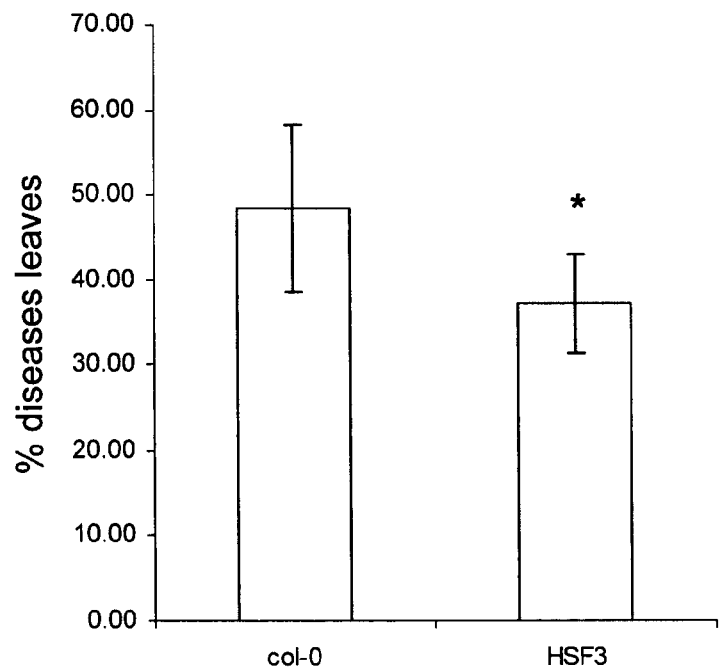
Figure 8B:
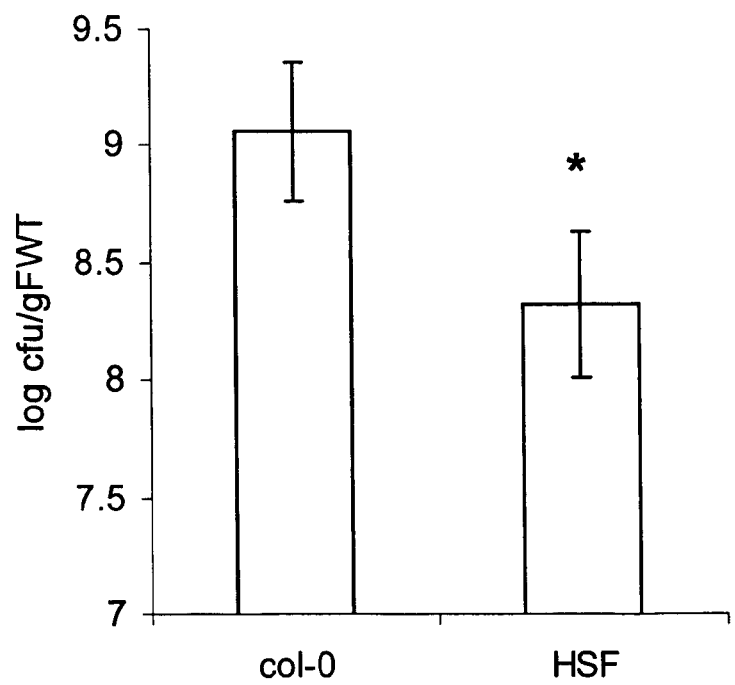

FIG. 8a shows wild type (col-0) and transgenic plants over-expressing Hsf3 infected with virulent *Pseudomonas syringae* pv. tomato DC3000. Diseased leaves were scored as those showing a yellowing 7 days after inoculation. FIG. 8b shows the number of bacteria (colony forming units) recovered after 5 days of infection. *=significant difference (p<0.05).

Figure 9A:
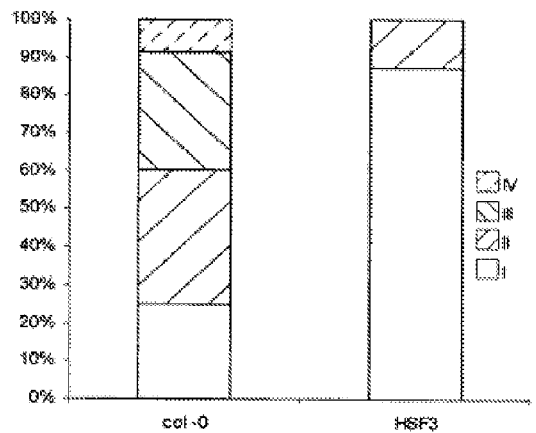
Figure 9B:
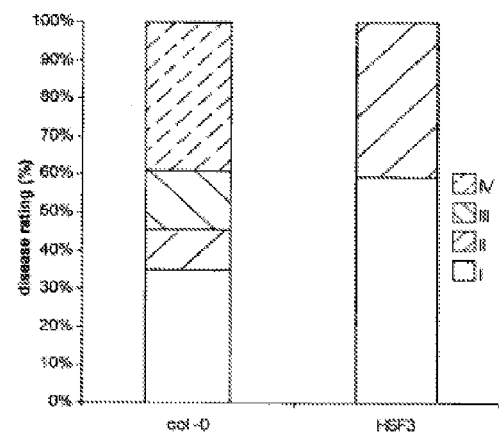
Figure 9C:
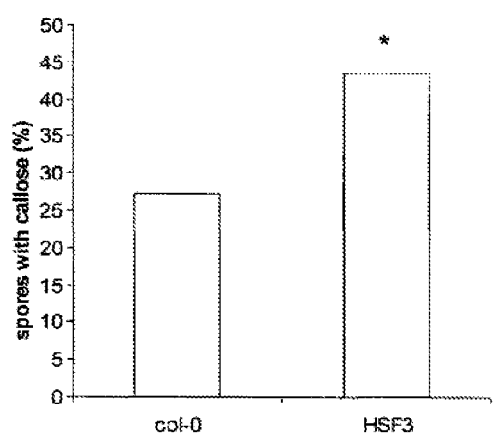
Figure 9D:
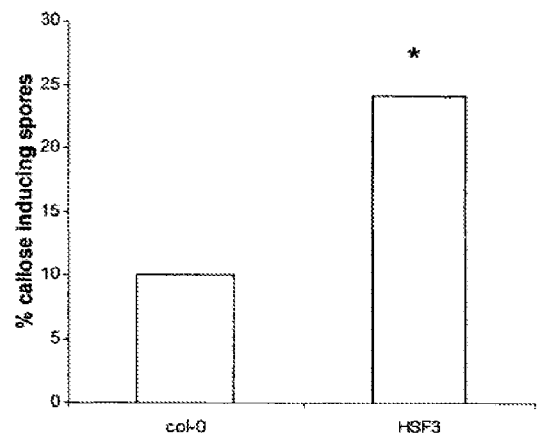

FIGS. 9a and 9b are bar graphs showing wild type and transgenic plants overexpressing Hsf3 infected with *Hyaloperonospora parasitica*. Disease symptoms were scored by different disease classes as follows: I healthy leaves, II chlorotic lesions, III leaves with sporulation and IV leaves with chlorotic lesions and sporulation. The HSF3 plants have mainly healthy leaves and at most leaves that show chlorotic lesions. The fungus is prevented from sporulating on HSF3 leaves. As shown in FIGS. 9c and 9d, callose deposition at pathogen entry point was scored using epifluorescence microscopy by counting the coincidence of spore presence and callose deposition. The more callose with spores the higher the resistance, as seen in the 35S-Hsf3 plants.

Figure 10:
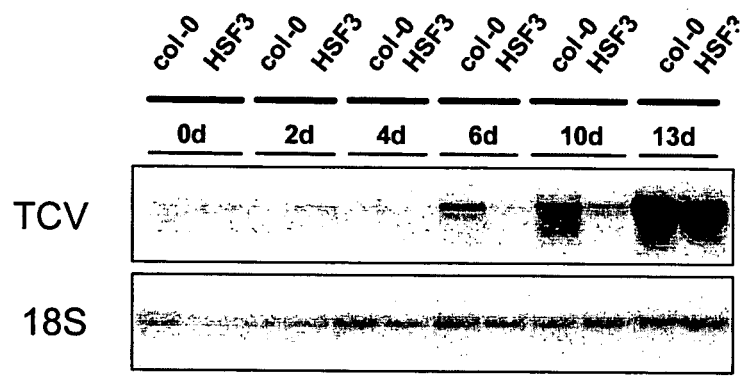

FIG. 10 Northern blot analysis. Wild type and transgenic plants overexpressing Hsf3 infected with turnip crinkle virus. Viral RNA accumulation in leaves of HSf3 plants is delayed compared with wild type.

Figure 11:
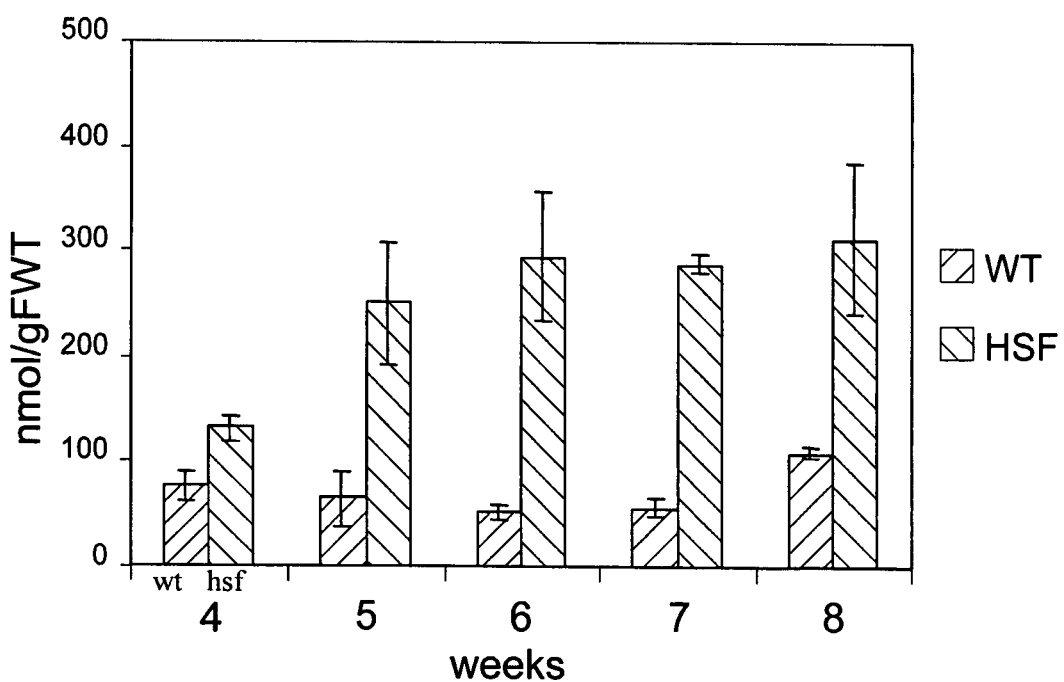

FIG. 11 shows foliar $H_2O_2$ levels during rosette development in 358-Hsf3 (HSF) and wild type plants (WT).

Figure 12:
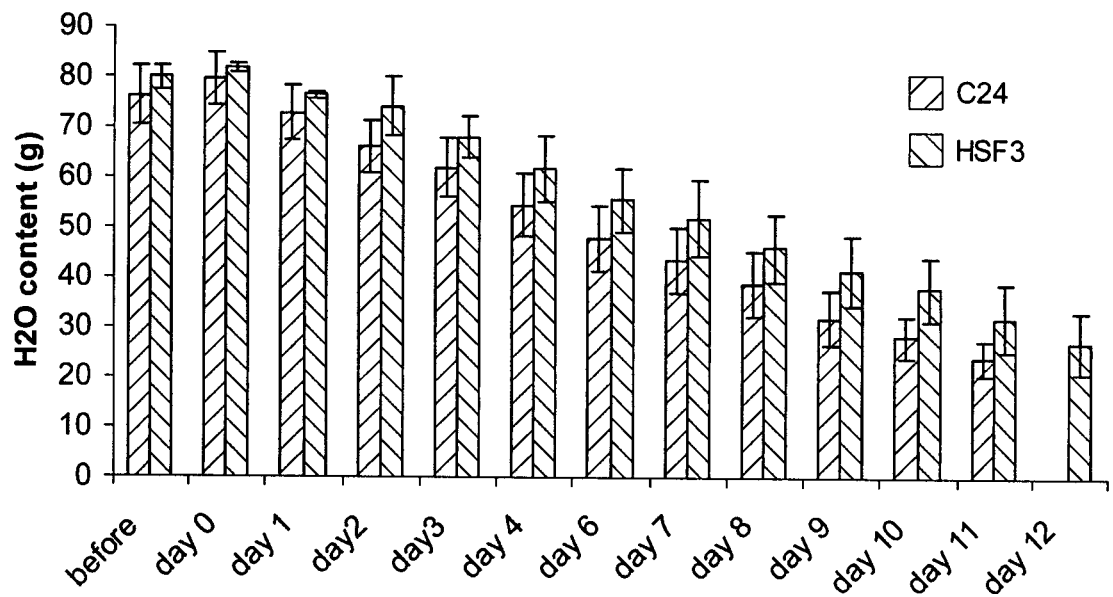

FIG. 12 shows a decline in pot water content for 35S-Hsf3 (HSF3) and wild type plants (C24) under drought conditions in a glasshouse. Withdrawal of water began at day 0.

Figure 13A:
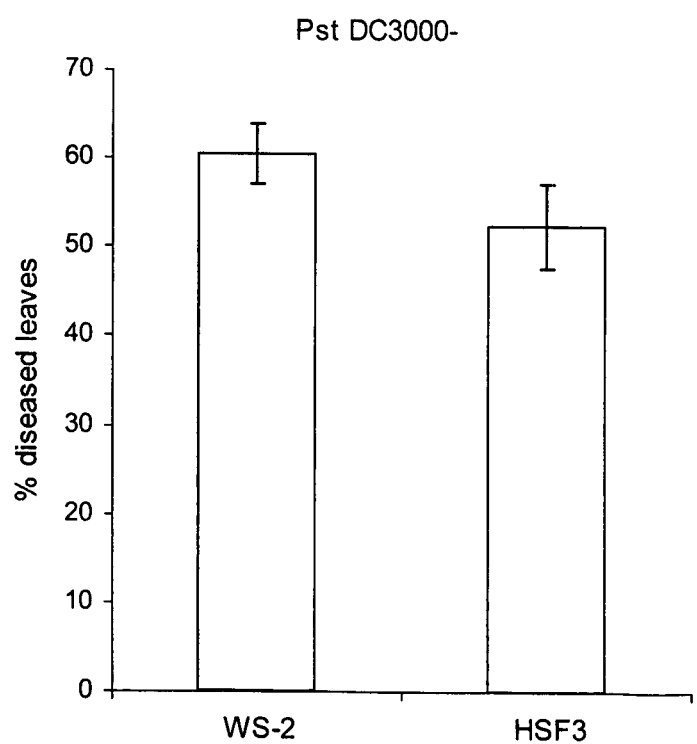
Figure 13B:
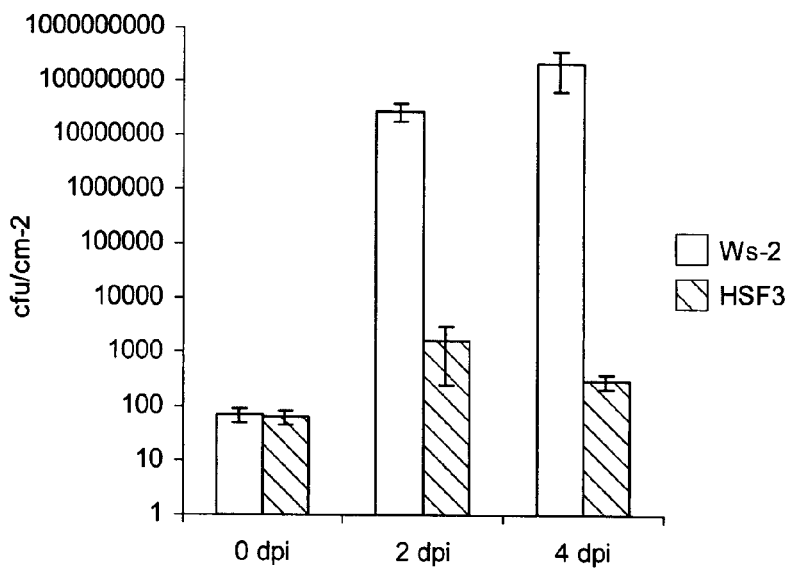

FIGS. 13a and 13b show a comparison of wild type and transgenic plants overexpressing Hsf3 infected with virulent *Pseudomonas syringae pv. tomato* DC3000. FIG. 13a shows diseased leaves scored as those showing a yellowing 7 days after inoculation. FIG. 13b shows number of bacteria (cfu/$cm^2$) recovered after 5 days of infection.

Figure 14A:
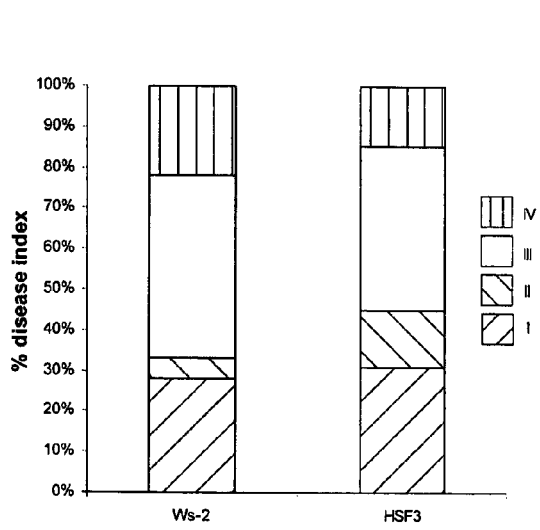
Figure 14B:
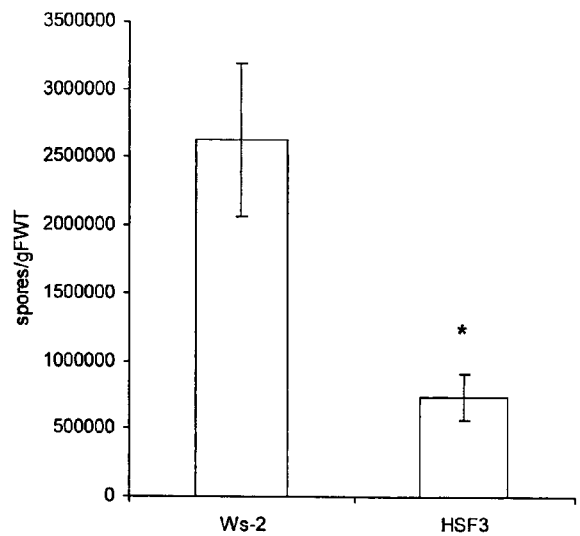
Figure 14C:
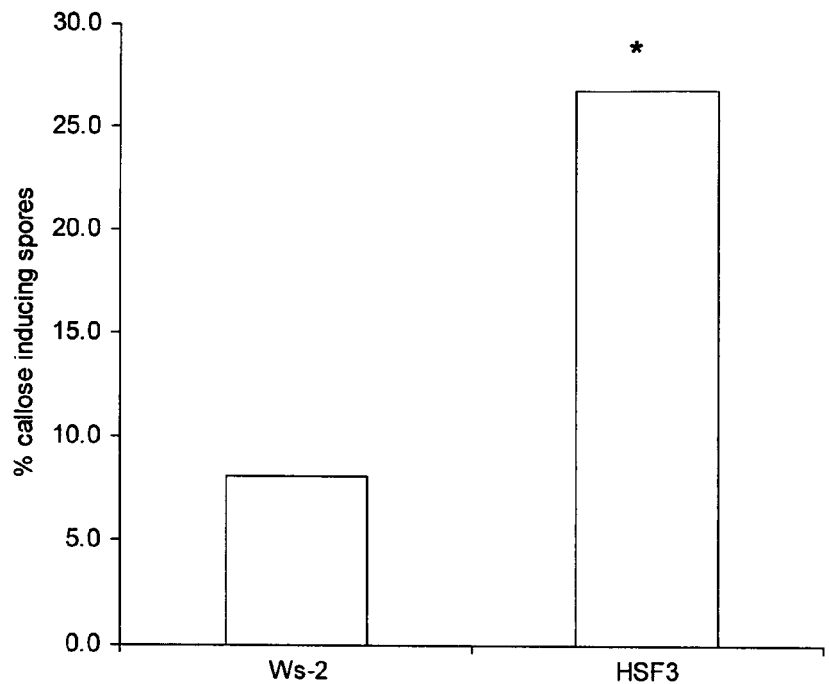

FIGS. 14a to 14c are bar graphs showing wild type and transgenic plants overexpressing Hsf3 infected with *Hyaloperonospora parasitica. Disease symptoms were scored by different disease classes as follows: I healthy leaves, II chlorotic lesions, III leaves with sporulation and IV leaves with chlorotic lesions and sporulation. The fungus is prevented from sporulating on HSF3 leaves as shown in FIG. 14b. FIG. 14c shows callose deposition at pathogen entry point scored using epifluoresnce microscopy by counting coincidence of spore presence and callose deposition.

Figure 15:
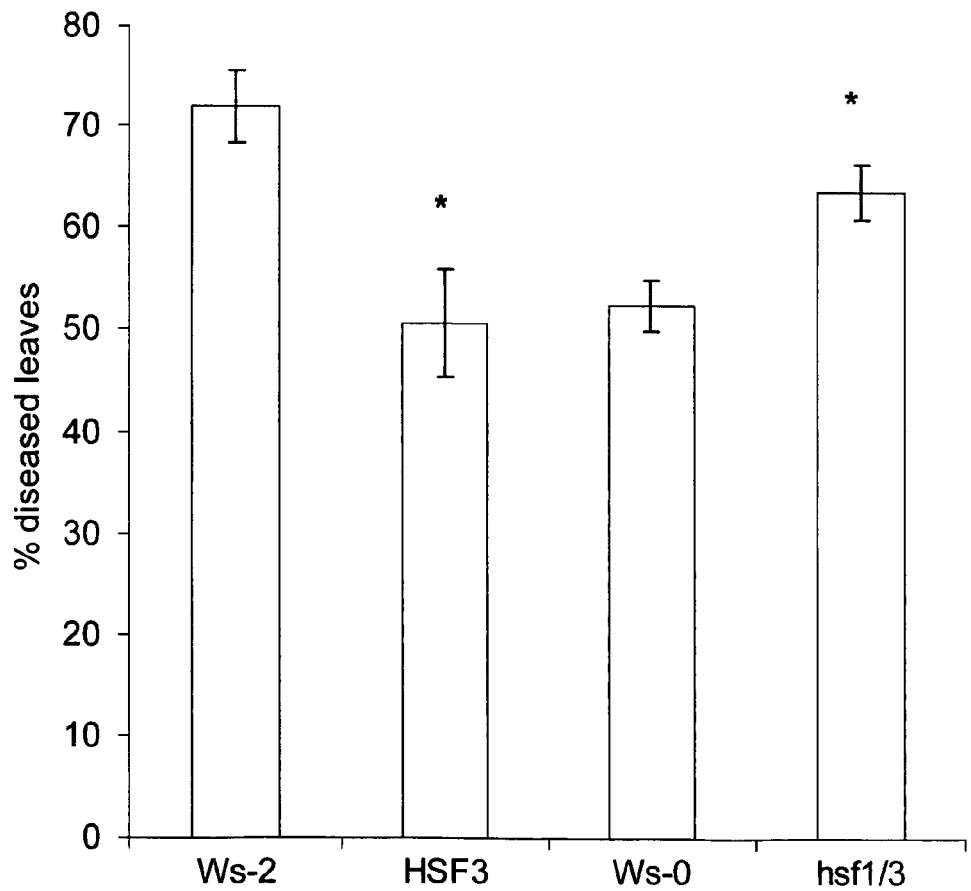

FIG. 15 compares wild type and transgenic plants overexpressing Hsf3 infected with virulent Pseudomonas svringae pv. tomato DC3000 DC3000. Diseased leaves were scored as those showing a yellowing 7 days after inoculation. * = significant difference (p<0.05).

Figure 16:
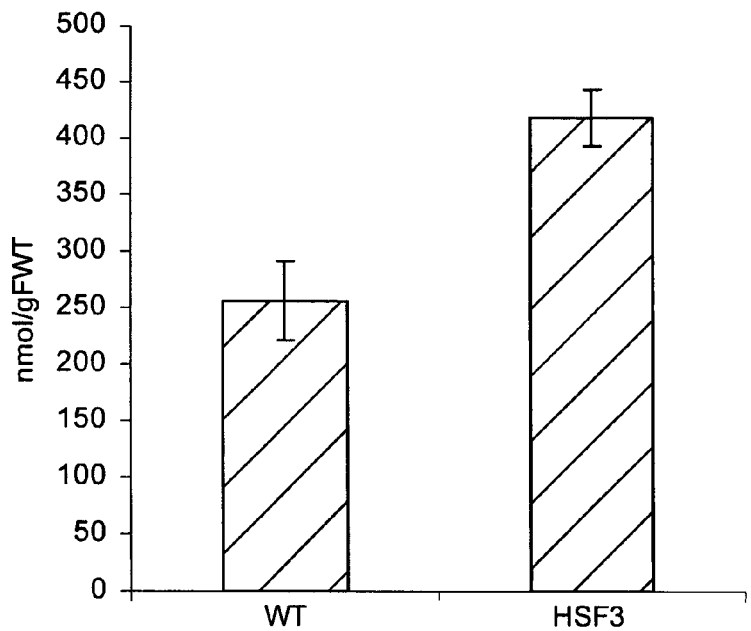

FIG. 16 shows foliar $H_2O_2$ levels during rosette development in 358-Hsf3 and wild type plants.

Figure 17:
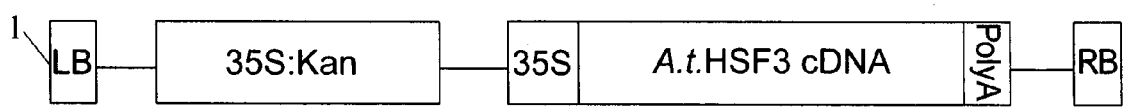

FIG. 17 is the expression construct used to transform Brassica napus.

Figure 18:
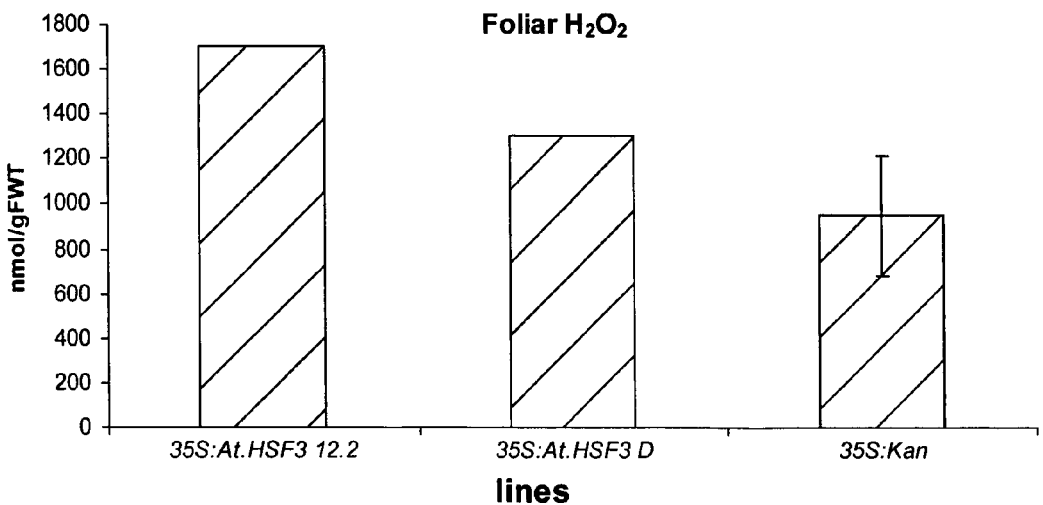

FIG. 18 shows a measurement of $H_2O_2$ of primary Brassica napus transgenics transformed with the construct as shown in FIG. 17

Figure 19:
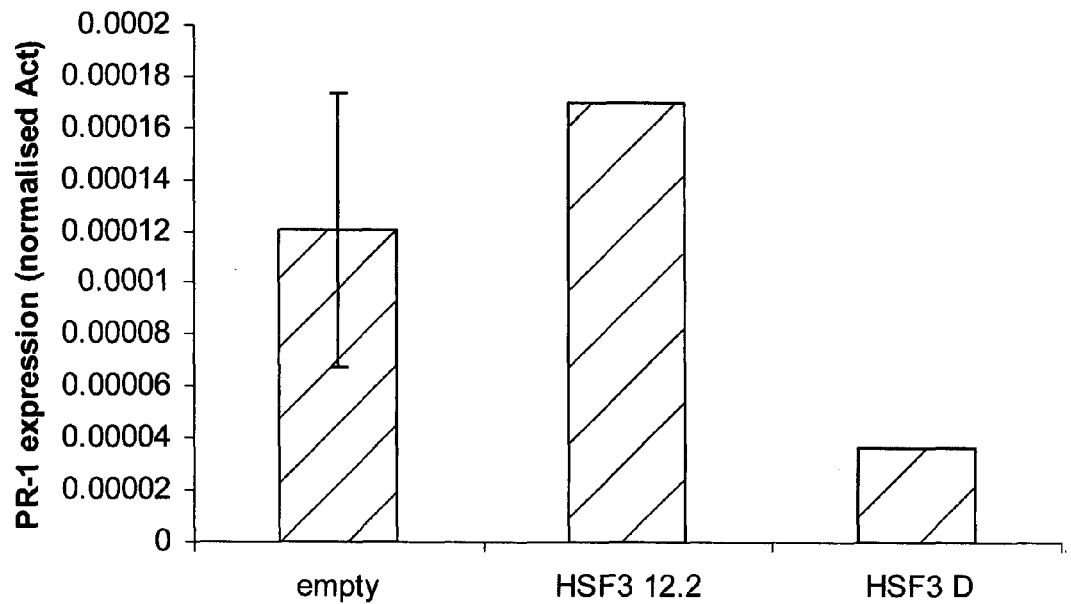

FIG. 19 shows that PR1 gene expression is significantly higher in the 35S:HSF3 12.2 line compared with controls. Gene expression data was analysed in the primary Brassica napus transgenics transformed with the construct as shown in FIG. 17 using qRT-PCR.

Figure 20:
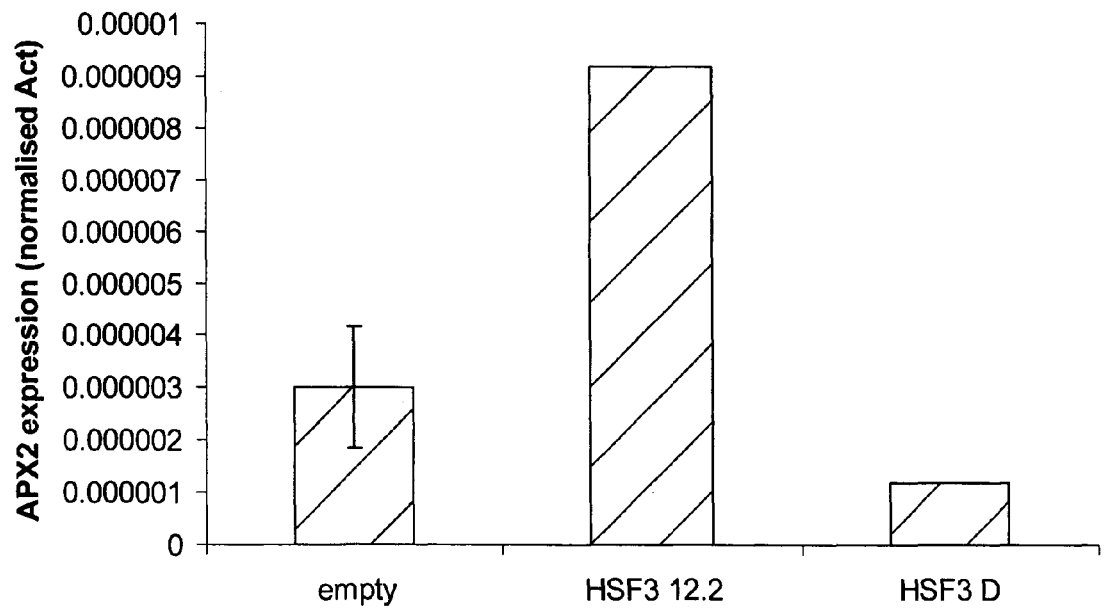

FIG. 20 shows APX2 gene expression in Brassica napus transgenics transformed with the construct as shown in FIG. 17.

EXAMPLES

35S-Hsf3 (35SAthsfA1b) plants display a number of characteristics which can be classified into two major traits, both elicited by overexpression of AtHsf3 and which interact to improve water productivity of these plants.

The plants show altered growth and development under well-watered conditions that mimic plants growing under mild water deficit conditions. Under a range of water deficit conditions these characteristics ensure that Hsf3 plants outperform wild type plants in terms of seed yield and survival. Plants show increased biomass of reproductive structures and seed production at the expense of leaf biomass, under both well-watered and drought conditions. The early flowering of Hsf3 plants under both well-watered and drought stress, altered senescence of source leaves and the consequent maintenance of photosynthetic efficiency are key factors in the increased seed yield of 35S-AtHSF3 plants under both well-watered conditions and a range of soil water deficit conditions.

35S-AtHsf3 (35SAthsfA1b) plants also show reduced transpiration. An elevated apoplastic $H_2O_2$ level in plants over-expressing Hsf3 may, in part, be responsible for the trait by altering stomatal guard cell function such that water loss through stomatal pores is reduced. $H_2O_2$ produced in guard cells has been implicated in the ABA signal transduction pathway leading to stomatal closure. Without wishing to be bound by theory, the inventors suggest that apoplastic $H_2O_2$ from elsewhere in the leaf can also influence guard cell function. Importantly, in these plants reduced rates of transpiration did not lead to a sufficiently reduced $CO_2$ assimilation rate as to reduce growth and yield.

Example 1

Creating a Construct and Transforming Plants

The creation of the plant described here has been published (Prandl et al 1998). Briefly, a full length 1.7 kb cDNA fragment containing the entire Hsf3 coding sequence was inserted as a BamH1 fragment into the binary Ti vector pB1121, base on the well-known vector pBIN19. This procedure fused the cDNA to the CaMV 35S promoter. The mRNA would also contain a GUS coding sequence followed by a nos polyadenylation sequence. Moncistronic constructs fused to 35S promoter have also been created for transformation into crop plant species.

Example 2

Plant Growth in Response to Drought and Well Watered Conditions

Figure 2:
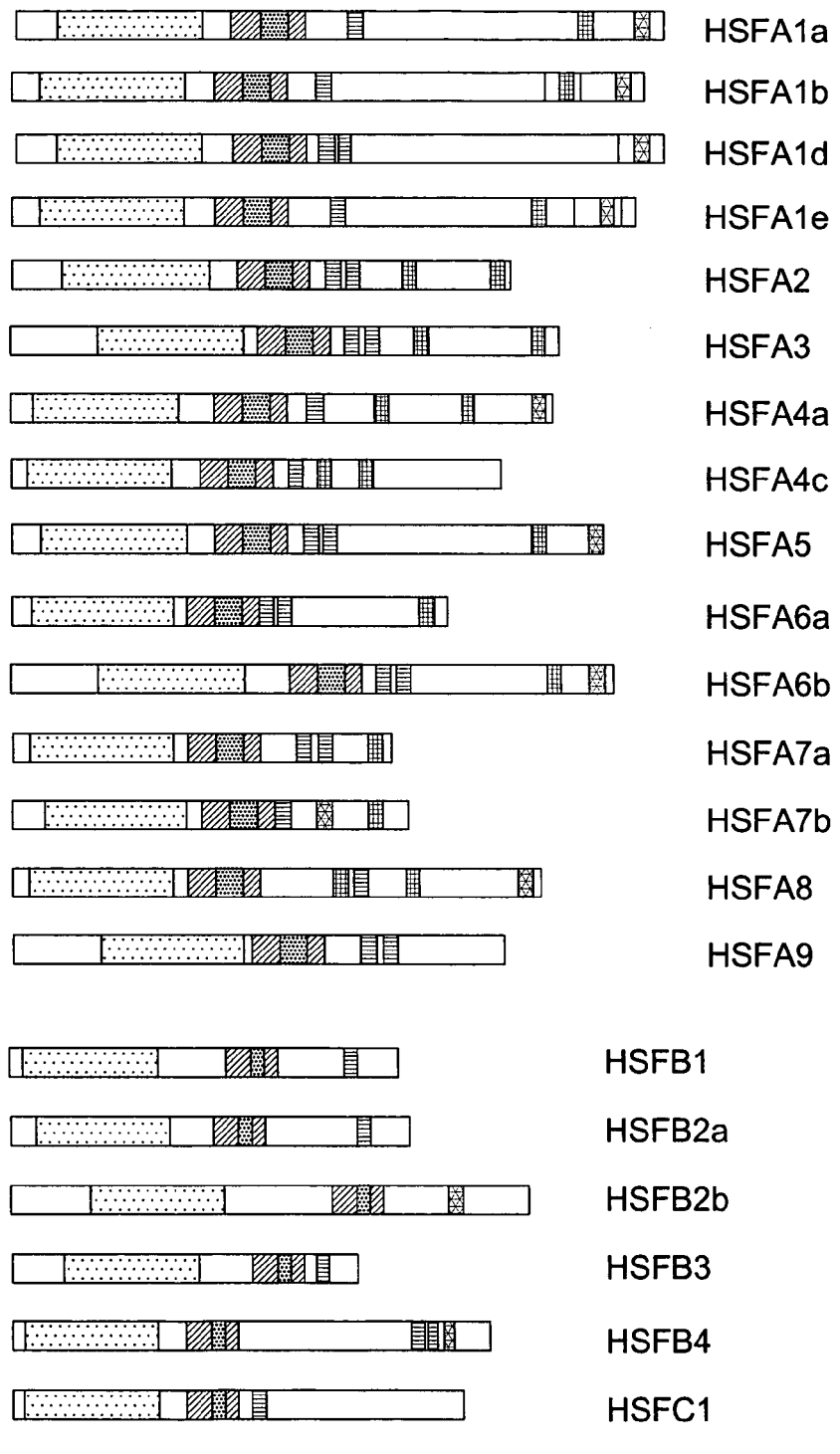
FIG. 2 shows the conserved domains of *Arabidopsis* Hsfs.
Figure 3:
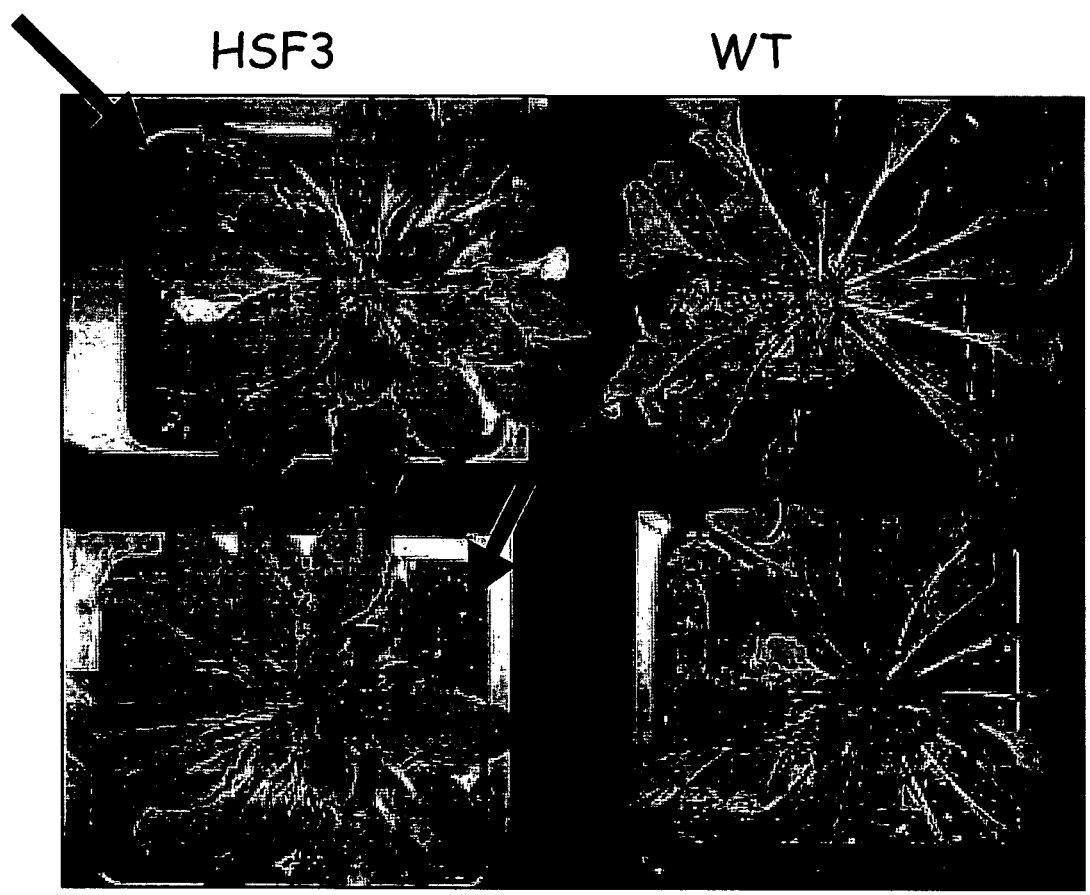
FIG. 3 shows wild type and 35S-Hsf3 (left) plants which were not watered for 2 weeks. Transgenic plants are marked with an arrow.

Plants were grown in controlled environment rooms under short day (8 h light/16 h dark) at 22° C. and 60% relative humidity. The Wild type (right) and 35S:AtHSF3 (left) plants are shown in FIG. 3. The plants were not watered for 2 weeks in a controlled environment room. These plants were typical in their response.

As shown in FIG. 4, the 35S AtHSF3 plants recover sufficiently from prolonged drought stress so that upon re-watering they flower and set seed. Wild type plants do not recover.

It was also shown that 35S-AtHSF3 plants have higher leaf temperatures. Under well-watered conditions, 35S-AtHSF3 plants have a 1.5-2.5° C. higher leaf temperature, implying a reduced transpiration rate and a lower stomatal conductance.

Plants were grown in individual pots for 4 weeks in the controlled environment room as described above. After 4 weeks plants were transferred to the glass house under long day and water was withdrawn for half of the pots. The plants were left to dry out to a similar soil water content of ~35% and were then re-watered.

When control and 35S-AtHsf3 plants were re-watered at the times indicated in FIG. 5, seed yield was substantially higher in 35S-AtHsf3 plants than wild type (WT) plants (Table 3), a differential that was also observed in watered controls (Table 3). Since the amount of water provided was the same, these data represent a real increase in water productivity of the 35S-AtHsf3 plants compared with WT control. Thus, 35S-AtHsf3 plants have a higher seed yield in well-watered conditions and after a mild water deficit stress.

TABLE 3

Total seed yield from plants subjected to drought in a containment glasshouse.

| Genotype | Treatment | Seed Yield (mg plant[1]) | n | P |
| --- | --- | --- | --- | --- |
| 35S-AtHSF3 | Watered | 361 ± 84 | 4 | 0.022 |
| WT | Watered | 156 ± 86 | 4 | |
| 35S-AtHSF3 | mild water deficit | 368 ± 31 | 4 | 0.0005 |
| WT | mild water deficit | 156 ± 38 | 4 | |

The water stress conditions were those applied in FIG. 5a up to the times indicated, when re-watering started. Controls were kept well-watered throughout the experiment.

Furthermore, rosette and reproductive structure biomass was measured. This was done by at the end of the life cycle. Plants were bagged and these bags contained all stem, pods, seeds etc above the rosette. The rosettes were harvested and bagged separately. The seed was threshed from the stems. All chaff was collected. The chaff, rosettes and soil pots were placed in a drying oven at 70 degrees Celsius for 72 hrs. These were weighed. Seed was weighed and counted. Dry weight measurements of the above ground vegetative (rosette) and reproductive (stalks and pods) parts and seed yield were determined under two different soil water contents. (see FIG. 7)

The experiments shows that 35S-AtHsf3 rosette biomass was reduced but the biomass of all aerial parts was increased in the same plants.

Example 3

Measurement of Photosynthetic Electron Transport

This was done by measuring the maximum efficiency (Fv/Fm) of photosystem II. Whole rosette or leaf Fv/Fm values were taken to indicate their response to the drought treatment using a chlorophyll a fluorescence imaging system (Fluorimager; Technologica Ltd, Colchester, UK) as described by Barbagallo et al 2003.

$CO_2$ gas exchange measurements were carried out on leaves of 5 week old plants using a CIRAS-2 (PP systems, Hitchin, U.K) CO2/H2O Infra Red Gas Analyser. Photosynthetic electron transport rates higher in drought-stressed 35S-AtHSF3 plants. The quantum efficiency of photosynthetic electron transport showed no difference between the genotypes in watered conditions, but was 15% better after 11 days of drought in 35S-HSF3 versus wild type (see FIG. 5b). There were no differences between 35S-AtHSF3 and wild type in the response of photosynthetic $CO_2$ exchange to intercellular $CO_2$ concentration when well watered. These parameters were used to evaluate transgenic plants.

Example 4

Measurement of Flowering

Growth conditions were as described earlier. The first 4 weeks plants were grown in controlled environment rooms after which plants were transferred to the glass house and water level was maintained at either 40% or 80% soil water content. Measurement of flowering time was done by noting the time of the visible (by naked eye) of first appearance of the floral apical meristem as the number of days post germination until the terminal flower opened. 35S-Hsf3 plants fully flowered (terminal flower open) on average 7 days earlier than the Col-0 plants.

It was shown that 35S-AtHsf3 plants showed on average 7 days early flowering. During flowering and seed set, leaves of 35S-AtHSF3 plants show delayed senescence until siliques yellowed under glasshouse conditions. This may mean that in 35S-Hsf3 flowering plants, source leaves could maintain a supply of photosynthate to ensure an increased reproductive biomass and the supply to developing seed for longer, and this was a contributing factor for the observed increase in seed yield in 35S-AtHsf3 plants, and reproductive biomass.

Example 5

Measurement of $H_2O_2$ Content 100 mg of leaf material was extracted in 0.1M HCl and the supernatant of this extraction was purified using activated charcoal. Analysis of $H_2O_2$ levels was by spectrophotometry using the Amplex Red kit from Invitrogen. It was shown that the 35S-AtHsf3 plants have up to 3 times the foliar $H_2O_2$ content of wild type plants. This increased $H_2O_2$ accumulates only in the apoplast and is generated by enhanced activity of apoplastic reticuline (carbohydrate) oxidase. The enhanced $H_2O_2$ levels stimulate an increase in both ascorbate peroxidase and cell wall peroxidase activities.

Example 6

Measurement of ABA Content 1 g of leaf material was harvested and extracted in methanol. The supernatant of this extraction is dried down and samples were dissolved in diethylether/methanol. The diethylether phase is put through a $NH_2$ SPE column and washed subsequently with chloroform/isopropanol before resuspending in diethylether and acetic acid. Analysis of ABA content was carried out using Gas chromatography combined with mass spectrometry (GC/MS) adapted from a method described by (Muller et al 2002).

The experiments showed that ABA content is no different from wild type plants under well-watered conditions and significantly our microarray data show no alteration of ABA-responsive genes (other than APX2).

Example 7

Microarray Experiment

Rosettes from 5 week old Col-0 and HSF3 plants were harvested and RNA was extracted from 2 different biological samples. Gene expression analysis was carried out using *Arabidopsis* 3 whole genome oligonucleotide-based microarrays from Agilent cRNA labelling and hybridisation of the arrays was according to the manufacturers' instructions.

TABLE 4

| Name | Locus | Classification | Hsf3/WT fold change |
|---|---|---|---|
|  | At5g03720 | At-HSFA3 | 3.3 |
| HSF4 | At4g36990 | At-HSFB1 | 2.5 |
| HSF5 | At1g67970 | At-HSFA8 | 2.1 |
| HSF6 | At5g62020 | At-HSFB2a | 2 |

Example 8

Pathogen Infections

*Pseudomonas syringae* pv tomato (DC3000-) infection was carried out on 5 week old plants. Whole rosettes were dipped in a solution containing $5*10^7$ colony forming units (cfu)/ml. Leaf material was harvested at the beginning (day 0) and 5 days post inoculation to determine the bacterial proliferation by grinding in MgSO4 and plating a dilution series on KB plates containing Rifampicin (50 mg/L) and Cycloheximide (100 mg/L). Bacterial proliferation is calculated as the difference in cfu between day 5 and day 0. Symptoms were scored 6 days post inoculation (yellowing leaves).

*Hyaloperonospora parasitica* infection was carried out at a concentration of $5*10^4$ spore/ml. The fungal spores are obtained from leaves of infected plants and are extracted in water and diluted to the right concentration. Leaves of 3 week old plants are inoculated with the fungus by spraying a fine layer of liquid onto each leaf. Disease symptoms and callose formation are scored 7 days post inoculation.

Turnip crinkle virus infection was carried out on 3 week old plants. 2.5 ul of 0.1 ug/ul viral RNA in bentonite buffer were gently rubbed into three leaves of each plants. Systemic leaves are harvested at different times post inoculation and RNA is extracted and checked for viral RNA replication via Northern blotting. As a loading control, the blot is probed with 18S rRNA.

Example 9

Rapeseed (*Brassica napus*), also known as rape or oilseed rape, is a bright yellow flowering member of the family Brassicaceae (mustard or cabbage family). Rapeseed is grown for the production of animal feed, vegetable oil for human consumption, and biodiesel; leading producers include the European Union, Canada, the United States, Australia, China and India. In one set of experiments, a construct overexpressing HSF3 from *Arabidopsis* was used to transform rapeseed.

*Brassica napus* ecotype Q6 was transformed with a 35S:A.t.HSF3 construct and an empty vector control (35S:Kan) (see FIG. 17). Eight months post transformation, 7 empty vector plants and 2 HSF3 transformed lines were recovered onto soil. Transformants were screened for the presence of the transgene using a 35S forward and HSF3 reverse primer, using 35S: Kan, empty vector controls and *Arabidopsis* HSF3 plant DNA as a positive control. Only one of the HSF3 transgenics (35S:HSF3 12.2) amplifies the 35S-HSF3 junction PCR product. The empty vector controls are also negative.

$H_2O_2$ of primary transgenics was measured (see FIG. 18). Foliar $H_2O_2$ levels are increased in line 35S:HSF3 12.2 compared to the empty vector controls.

Stomatal conductance and photosynthetic rate of the primary transgenics were also measured. Stomatal conductance is reduced in the 35S:HSF3 12.2 plant. Despite their reduction in stomatal conductance, the linear phase of photosynthesis is not affected in the 35S:HSF3 12.2 plants, however, photosynthesis saturates at lower levels compared to the empty vector controls and the second HSF3 line.

We also analysed the transgenic plants by thermal imaging of primary transgenic lines of oils seed rape. It was found that the HSF3 transgenic (35S:HSF3 12.2) shows a 1° C. warmer leaf temperature across the plant compared with flanking empty vector controls. This indicates less evaporative water loss by transpiration in the HSf3 transgenic compared with controls. This agrees with the lowered stomatal conductance values for the same line and is consistent with the observations made in 35S:HSF3 *Arabidopsis* plants.

Furthermore, gene expression data was analysed in the primary transgenics using qRT-PCR. PR1 gene expression is significantly higher in the 35S:HSF3 12.2 line compared with controls. This indicates activated pathogen defences.

We also analaysed APX2 gene expression. Increased expression in the 35S:HSF3 12.2 line shows functioning HSF3 and, from a physiological point of view, again indicates a change in leaf water status.

The data demonstrates that transformation of *Brassica napus* with a 35S:A.t.HSF3 construct overexpressing HSF3 from *Arabidopsis* produces similar results to those observed when overexpressing HSF3 from *Arabidopsis* in *Arabidopsis*.

LIST OF REFERENCES

Barbagallo et al 2003, *Plant Physiol.* 132, 485-493
Cook R J, 1998. PNAS. 95, 9711-9712.
Crute I R et al., 1996. The Plant Cell. 18, 1747-1755.
EEA 2000 Europe's environment: the third assessment. Chapter 8: Water. Copenhagen.
FAO 2003 Review of World Water Resources by Country. Water Reports 23, 123 pp. Rome:FAO.
Hu et at, 2006, PNAS 103, 35, 1287-12992
Kotak S et al., 2004. The Plant Journal 39, 98-112.
Miller G et al., 2006. Animals of Botany. 98, 279-288.
Morison J I L. et al. (2008) Proc Royal Society series B 363: 639-658.
Muller et al 2002, Planta 216, 44-56
Nover L et al., 2001 Cell Stress & Chaperones. 6, 177-189.
Panchuck I et al., 2002 Plant Physiology. 129, 838-853.
Panikulangara T et al., 2004. Plant Physiology. 136, 3148-3158
Parry M. A. J, et al 2005. Annals of Applied Biology 147, 211-226.
Prandl R et al 1998 Molecular and General Genetics 259: 269-278.
Qiang L et al., 2000. Chinese Science Bulletin. 45, 970-975.
Rijsberman, F. 2004 Water scarcity—fact or fiction? R. A. Fischer, N. Turner, J. Angus, L. McIntyre, M. Robertson, A. Borrell & D. Lloyd (eds) New Directions for a Diverse Planet. Proceedings of the 4th International Crop Science Congress, Brisbane, Australia, 26 Sep.-1 Oct., 2004.
Richards, R. A. 2004 Physiological traits used in the breeding of new cultivars for water-scarce environments. R. A. Fischer, N. Turner, J. Angus, L. McIntyre, M. Robertson, A. Borrell & D. Lloyd (Eds) New Directions for a Diverse Planet. Proceedings of the 4th International Crop Science Congress, Brisbane, Australia, 26 Sep.-1 Oct., 2004.
Sakuma Y et al., 2006. The Plant Cell. 18, 1292-1309.
Valliyodan B et al., 2006. Current Opinion in Plant Biology. 9, 1-7.

---

The invention claimed is:

1. A method of generating a plant having improved water productivity under non-drought and water deficit conditions, the method comprising
    (a) introducing to the plant and overexpressing in the plant a polynucleotide comprising a sequence encoding a Class A plant heat shock factor (Hsf), thereby producing a transgenic plant;
    (b) exposing the transgenic plant to non-drought conditions or water deficit conditions; and
    (c) assessing the yield produced from the transgenic plant per unit of water consumed, wherein a greater yield, relative to that of a corresponding wild type plant, indicates the generation of a plant having improved water productivity under non-drought and water deficit conditions.

2. The method of claim 1, wherein the non-drought conditions are mild water deficits.

3. The method of claim 1, wherein the water deficit conditions are drought conditions.

4. The method of claim 1, wherein the plant is a cereal plant.

5. The method of claim 1, wherein the plant is maize, wheat, rice, oilseed rape, sorghum, soybean, cotton, potato, tomato or poplar.

6. The method of claim 1, wherein the Class A plant Hsf is an *Arabidopsis* plant Class A Hsf.

7. The method of claim 6, wherein the *Arabidopsis* plant Class A Hsf is AtHsfA1a, AtHsfA1b, AtHsfA1d, AthsfA1e, AtHsfA2, AtHsfA3, AtHsfA4a, AtHafA4c, AtHsfA5, AtHsfA6a, AtHsfA6b, AtHsfA7a, AtHsfA7b, AtHsfA8 or AtHsfA9.

8. The method of claim 7, wherein the *Arabidopsis* plant Hsf is AtHsfA1b or AtHsfA1a.

9. The method of claim 1, wherein the Class A plant Hsf is a tomato plant Class A Hsf.

10. The method of claim 6, wherein the Class A plant Hsf is the *Arabidopsis* plant Hsf AtHsfA1b, which is represented by SEQ ID NO:1.

11. The method of claim 6, wherein the *Arabidopsis* plant Hsf is AtHsfA1b, which is represented by SEQ ID NO:1.

* * * * *

SEQUENCE LISTING

```
<160> NUMBER OF SEQ ID NOS: 1

<210> SEQ ID NO 1
<211> LENGTH: 2481
<212> TYPE: DNA
<213> ORGANISM: Arabidopsis thaliana

<400> SEQUENCE: 1
gagagagtct ctgtctctgt aaaagatatt tgagcttgag aagaacagaa gaaacttcca      60
ggatcaatca atcgatcaac tttagtgaac taactcttga tttttcattc gaagttatgg     120
aatcggttcc cgaatccgta ccatcgccga actcgaatac accgtcaata ccaccgccgg     180
tgaactccgt accgcctttc ttgagtaaaa cctacgacat ggttgatgat ccgttgacca     240
atgaggtcgt ttcgtggagc agcgggaaca acagcttcgt cgtctggagt gccccggagt     300
```

```
tctcgaaggt gctcttgccc aagtatttca agcacaacaa cttctccagc ttcgtcagac      360
agttaaatac ttatgtaagc atcatttttt gtgttattgt caatttattt ttctagaaat      420
tgatcgtttt ttcgtggtac aatttgggga acatcgtgaa atgttgaagg gttctagtct      480
tagtgactag atccatggat gtgttggatt attttttaaag ccatatcaat ctgtctactc      540
atcaaaagat tccacagaac tttgcaggcg cactgtcaca tatgtctgaa gattgtttcc      600
tcaattgttt tctgccttgt agctctaaca aaacagaatg tctatcagtt gtctgaacat      660 tagcttgtt ttcatttgta tatttccgtc caggtacact ttttgataa actaagaact      720 attactttcc ttataacatg gtgattttgt gctacaccca agcatagtgt ggagaatttg      780
tttacttctc aaactttgct ataactagaa catataacta atctggtctg ttttctagtc      840
tacctgttta atgtttatac attttttgtac aattgcgcta tgttggcttt tcttcttccc      900
ctaaattcaa gcaacatcgt ttcagttctt caatttgaat ttcgatattt atgatagcct      960
ctctgtattc tgatgtccag ggtttcgaaa aagttgatcc tgaccgatgg gaatttgcaa     1020
atgaaggatt tcttagaggc cgaaaacaac tactgaagag tattgtcagg agaaaacctt     1080
cgcatgtgca gcagaatcag caacaaactc aagttcagag ctcatctgtt ggtgcttgtg     1140
tcgaggtggg gaagtttgga atagaagaag aagtggaaag acttaagcgg gataagaatg     1200
ttcttatgca agaactcgtc aggttaaggc agcaacagca agctactgaa aaccaactgc     1260
agaatgtggg acagaaagtt caggtgatgg agcaaaggca acaacaaatg atgtcgtttt     1320
tagcaaaggc tgttcaaagt ccaggtttct taaaccagtt agtacaacag ataataatg      1380 atggcaacag acaaattcca ggaagcaaca aaagaggag acttcctgta gatgagcagg      1440
agaatcgtgg tgacaatgtg gctaatggtc ttaaccgcca gattgttaga tatcagccgt     1500
cgataaacga agcagcacaa atatgcttc gacagttctt aaatactagt acctcacctc     1560
ggtatgaatc agtttcaaac aatcctgaca gtttcctatt gggtgatgtt cccagttcta     1620
cctctgtaga caatgggaac ccttcaagta gagtttctgg agtaacattg gccgagtttt     1680
cacccaacac agttcagtca gcaacgaatc aagtacccga agcaagtttg gctcatcatc     1740
ctcaagctgg tctggttcag ccaaatatag gtcaaagtcc ggctcaagga gcagcacctg     1800
cagactcttg gagccctgaa tttgatttag ttggatgcga gacagatagt ggagagtgtt     1860
ttgatccaat aatggctgtt ttagatgagt cagaaggcga tgcaatttct cctgaaggtg     1920
agggcaagat gaatgagtta ctggagggag tccctaagct gccccggaatc caagatccat     1980 tctgggaaca gttcttttct gttgaactcc agcgattgc agatacagac gatattctat      2040
caggatcagt ggagaataat gacttggtat tggaacaaga accaaacgag tggacccgta     2100
atgaacaaca aatgaagtat cttactgaac aaatgggact gctttcctca gaagcacaga     2160
ggaaataaag gtaagaacat cgttaagttc aaacatgttt ctctgcattg ttgtatatct     2220
tgagagttat caattgtctc tcacaatgta gattttcagg ggaggttgca aaaggagata     2280
tgaaggaacg aggaatatat cagatggtgt gtatacccct tacatttta cttaaatgaa      2340 aaaaaaacag agagaagaaa cataaaagat ttaccaccaa gcttgtgaat agttagtaga     2400
gatcggtttt tgtgttgttt atattatact tttgtgtgaa aacgttcatc ttgttcaatt     2460
atcatctcac tagtacggta a                                               2481
```